US012721927B2

(12) United States Patent
Anthis et al.

(10) Patent No.: US 12,721,927 B2
(45) Date of Patent: Sep. 1, 2026

(54) KIT COMPRISING ADHESIVE HYDROGEL AND IMPREGNATING FLUID

(71) Applicants: EMPA EIDGENÖSSISCHE MATERIALPRÜFUNGS-UND FORSCHUNGSANSTALT, Dübendorf (CH); ETH ZURICH, Zürich (CH)

(72) Inventors: Alexandre Anthis, Zürich (CH); Inge Herrmann, Seiben/Wangen (CH); Tino Matter, Zürich (CH)

(73) Assignees: EMPA EIDGENÖSSISCHE MATERIALPRÜFUNGS- UND FORSCHUNGSANSTALT, Dübendorf (CH); ETH ZÜRICH, Zürich (CH)

( * ) Notice: Subject to any disclaimer, the term of this patent is extended or adjusted under 35 U.S.C. 154(b) by 345 days.

(21) Appl. No.: 18/272,687

(22) PCT Filed: Jan. 19, 2022

(86) PCT No.: PCT/EP2022/051137
§ 371 (c)(1),
(2) Date: Jul. 17, 2023

(87) PCT Pub. No.: WO2022/157198
PCT Pub. Date: Jul. 28, 2022

(65) Prior Publication Data

US 2024/0299614 A1 Sep. 12, 2024

(30) Foreign Application Priority Data

Jan. 19, 2021 (EP) ..................................... 21152240

(51) Int. Cl.
*A61L 24/00* (2006.01)
*A61L 24/04* (2006.01)
(Continued)

(52) U.S. Cl.
CPC ......... *A61L 24/0031* (2013.01); *A61L 24/001* (2013.01); *A61L 24/0015* (2013.01);
(Continued)

(58) Field of Classification Search
CPC ............. A61L 24/0031; A61L 24/0015; A61L 24/001; A61L 2300/404; A61L 2300/102;
(Continued)

(56) References Cited

U.S. PATENT DOCUMENTS

| | | |
|---|---|---|
| 10,149,992 B2 | 12/2018 | Pigeon |
| 2002/0147386 A1 | 10/2002 | Poff et al. |
| 2003/0100380 A1 | 5/2003 | D'Eath |
| 2006/0015083 A1 | 1/2006 | Munro et al. |
| 2008/0102029 A1 | 5/2008 | Fritz et al. |

(Continued)

FOREIGN PATENT DOCUMENTS

| | | |
|---|---|---|
| CN | 109106974 A | 1/2019 |
| EP | 4 029 536 A1 | 7/2022 |

(Continued)

OTHER PUBLICATIONS

Ryu et al., "Multipurpose Intraperitoneal Adhesive Patches," Advanced Functional Materials, 2019, vol. 29, 1900495, pp. 1-10.

(Continued)

*Primary Examiner* — Michele Kidwell
(74) *Attorney, Agent, or Firm* — Oliff PLC

(57) ABSTRACT

A kit of parts including two components, the first component being a patch including a non-degradable synthetic hydrogel and the second component being an impregnating fluid, which, upon in-situ polymerisation, anchors the patch on a tissue. The patch may include additional layers including sensing components or therapeutic components. In addition, the use of the kit of parts and the use of an impregnating fluid in surgery, in particular as suture or staple supports, e.g. suture or staple supports in the abdominal region such as intestinal anastomosis sites, or for sealing of artificial stoma.

15 Claims, 7 Drawing Sheets

Figure 1:
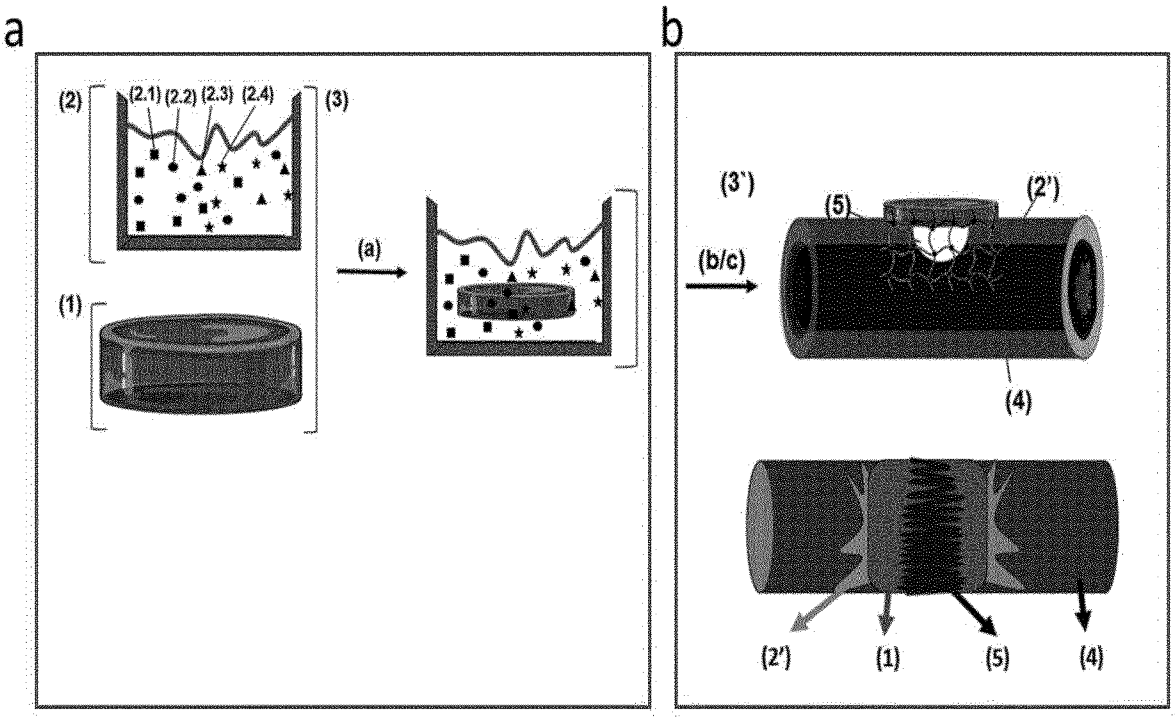

(51) Int. Cl.
*A61L 24/06* (2006.01)
*B33Y 80/00* (2015.01)

(52) U.S. Cl.
CPC ............. *A61L 24/046* (2013.01); *A61L 24/06* (2013.01); *B33Y 80/00* (2014.12); *A61L 2300/102* (2013.01); *A61L 2300/232* (2013.01); *A61L 2400/14* (2013.01)

(58) Field of Classification Search
CPC ......... A61L 2300/232; A61L 2300/414; A61L 2300/608; A61L 24/046; A61L 24/06; A61L 2400/14
See application file for complete search history.

(56) References Cited

U.S. PATENT DOCUMENTS

| | | | | |
|---|---|---|---|---|
| 2009/0280182 | A1* | 11/2009 | Beck | A61L 15/225 424/486 |
| 2011/0087271 | A1* | 4/2011 | Sargeant | A61B 17/0057 606/213 |
| 2013/0337566 | A1* | 12/2013 | Schmidt | C08J 3/075 435/404 |
| 2020/0116734 | A1 | 4/2020 | Chuang et al. | |
| 2020/0181426 | A1 | 6/2020 | Cao et al. | |
| 2024/0374781 | A1* | 11/2024 | Anthis | A61L 24/001 |

FOREIGN PATENT DOCUMENTS

| | | | | |
|---|---|---|---|---|
| WO | 2009/134414 | A2 | 11/2009 | |
| WO | 2014/105820 | A1 | 7/2014 | |
| WO | 2016/182444 | * | 11/2016 | A61C 13/00 |
| WO | 2018/106938 | A1 | 6/2018 | |
| WO | 2019/053269 | A1 | 3/2019 | |
| WO | 2021/250548 | A1 | 12/2021 | |

OTHER PUBLICATIONS

Li et al., “Tough adhesives for diverse wet surfaces,” Science, Jul. 28, 2017, vol. 357, pp. 378-381.

Blacklow et al., “Bioinspired mechanically active adhesive dressings to accelerate wound closure, ” Science Advances, Jul. 24, 2019, vol. 5, No. 7, eaaw3963, pp. 1-9.

Bouten et al., “The chemistry of tissue adhesive materials,” Progress in Polymer Science, 2014, vol. 39, pp. 1375-1405.

Montazerian et al., “Stretchable and Bioadhesive Gelatin Methacryloyl-Based Hydrogels Enabled by in Situ Dopamine Polymerization,” Applied Materials & Interfaces, 2021, vol. 13, pp. 40290-40301.

Suter et al., “Surgical Sealant with Integrated Shape-Morphing Dual Modality Ultrasound and Computed Tomography Sensors for Gastric Leak Detection,” Advanced Science, 2023, vol. 10, 2301207, pp. 1-14.

Dorkoosh et al., “Preparation and NMR characterization of superporous hydrogels (SPH) and SPH composites,” Polymer, 2000, vol. 41, pp. 8213-8220.

Cheng et al., “Multiwalled Carbon Nanotubes and NaYF4:Yb3+/Er3+ Nanoparticle-Doped Bilayer Hydrogel for Concurrent NIR-Triggered Drug Release and Up-Conversion Luminescence Tagging,” Langmuir, 2013, vol. 29, pp. 9573-9580.

Qureshi et al., “Environment sensitive hydrogels for drug delivery applications,” European Polymer Journal, 2019, vol. 120, 109220, pp. 1-39.

Kalidasan et al.,“ Wirelessly operated bioelectronic sutures for the monitoring of deep surgical wounds,” Nature Biomedical Engineering, Oct. 2021, vol. 5, pp. 1217-1238.

Apr. 19, 2022 International Search Report issued in International Patent Application No. PCT/EP2022/051137.

Apr. 19, 2022 Written Opinion of the International Searching Authority issued in International Patent Application No. PCT/EP2022/051137.

May 6, 2022 International Search Report issued in International Patent Application No. PCT/EP2022/051141.

May 6, 2022 Written Opinion of the International Searching Authority issued in International Patent Application No. PCT/EP2022/051141.

U.S. Appl. No. 18/272,705, filed Jul. 17, 2023 in the name of Alexandre Anthis et al.

Jun. 4, 2026 Office Action issued in U.S. Appl. No. 18/272,705.

* cited by examiner a b a b

KIT COMPRISING ADHESIVE HYDROGEL AND IMPREGNATING FLUID

The present invention relates to the field of surgery, in particular to suture and/or staple supports, e.g. suture and/or staple supports in the abdominal region, and sealants, e.g. for sealing of artificial stoma.

The invention provides a kit of parts comprising two components, the first component being a shaped article in the form of a patch comprising a non-degradable synthetic hydrogel and the second component being an impregnating fluid, which, upon in-situ polymerisation, anchors the patch on a tissue. The patch may comprise additional layers comprising sensing components and/or therapeutic components and/or a backing layer. The invention further provides for the manufacturing of such kits and the use of such kits. The invention further provides for the use of an impregnating fluid in a surgical method for adhering a patch to a sutured site, a stapled site or a stoma site of a subject in need thereof.

Many diseases, including colorectal cancers, bowel ischemia and inflammatory diseases such as Crohn's disease or ulcerative colitis, often require invasive surgical procedures.

Typically, such surgeries include removing or circumventing diseased tissue and connecting the remaining healthy tissue extremities by suturing or stapling, resulting in anastomosis sites. Such abdominal organ anastomoses can be accompanied by severe complications. Of these, anastomotic leakage is one of the most dreaded complications with reported incidence rates ranging from 4 to 21%, depending on the patient's condition (e.g. the patient's sarcopenia level) and the surgeon's experience. Reported mortality rates for patients suffering from anastomotic leaks range from 6 to 27%. In case of progression to septic peritonitis due to leaking of the bacteria-containing intestinal fluid, mortality rates as high as 50% have been reported.

While major efforts have focused on the prevention of such leaks, once established, their treatment is especially costly (usually more than 30,000 USD), and lengthy (usually more than 10 days in hospital). While numerous studies have investigated the adhesion properties of various surgical glues in dry, moist or wet environments under physiological conditions, there are only a few studies that have investigated the adhesion properties under conditions, where surgical sealants are exposed to non-sterile and/or chemically aggressive body fluids, such as intestinal fluid, intestinal content containing bacteria, and bile (Ryu et al., 2019).

Furthermore, the treatment of anastomotic leaks often requires the formation of temporary stomas and artificial drains to the patient's body for monitoring, adding to the societal burden that complications particularly during the healing of abdominal fistulas impose on the patient.

Li et al. [Science (2017), 357:378-381] describe a so-called "Tough adhesive" in the form of a pre-formed patch for adhesion to wet and dynamic surfaces, such as biological tissues. Such "tough-adhesives" consist of two layers: The first layer is an adhesive surface comprising a positively charged polymer (bridging polymer) interpenetrating a second hydrogel layer, wherein this latter second layer is a dissipative matrix, in particular an alginate-polyacrylamide hydrogel. Such tough adhesives are produced by applying a solution comprising the positively charged polymer along with coupling reagents on the dissipative matrix prior to application on a tissue, thereby forming an adhesive surface. In some cases, the "tough adhesive" was additionally bonded to a rigid polyethylene terephthalate (PET) film. Adhesion to the tissue is achieved by a combination of electrostatic interaction (positively charged polymer), covalent bonds (in particular through carbodiimide coupling mediated by the coupling reagents, i.e. 1-ethyl-3-(3-dimethylaminopro-pyl) carbodiimide (EDC), sulfated or unsulfated N-hydroxysuccinimide (NHS)) and physical interpenetration (i.e. limited penetration of the pre-formed bridging polymer into the tissue). The bridging polymers were selected from the group consisting of polyallylamine, chitosan, gelatin, polyethyleneimine and colla-gen. Thus, this document does not describe a kit of parts that includes an impregnating fluid comprising monomers that can be cured in-situ, thereby forming a mutually interpenetrating network (i.e. penetrating the tissue and the hydrogel support layer) which in turn fixates a patch on a tissue.

CN109106974 discloses a gel tissue plugging material that is intended for the use in wound healing and comprises a gel layer (substrate), a wet adhesion layer and optionally a backing layer. The gel layer comprises one or more polymers, preferably polymers derived from sodium alginate and/or polyacrylamide. The wet adhesion layer is present on at least one surface of the substrate in order to achieve adhesion to the tissue. The adhesion solution that is used to generate the wet adhesion layer comprises a polymer containing an amino group and may additionally comprise an activating factor (i.e. a coupling or crosslinking reagent), in particular carbodiimide, N-hydroxysuccinimide, genipin or an aldehyde compound. Thus again, the document does not describe an impregnating fluid comprising monomers that can be cured in-situ to form a mutually interpenetrating network in order to achieve adhesion of the patch to the tissue.

WO 2019/053269 describes an injectable alginate hybrid hydrogel, notably for the use in the treatment of fistulas and physiological leaks, in particular in the gastrointestinal tract. The hybrid hydrogel may be degradable or non-degradable. As exemplary described for the treatment of fistulas, the hydrogel polymers are injected into the fistula (treatment site) and subsequently gelation is initiated in situ through the addition of $Ca^{2+}$. Hence, the document does not describe a kit of parts comprising a shaped article in the form of a patch and again, does not describe an impregnating fluid comprising monomers that can be cured to a form mutually interpenetrating network in order to achieve adhesion of the patch to the tissue.

WO 2009/134414 describes devices, methods and kits for assisting in wound healing. The kits comprise an interpenetrating network (IPN) hydrogel, a wetting agent such as a saline solution, water or glycerol and instructions for pre-wetting the hydrogel with the wetting agent. The IPN hydrogel is pre-wetted with the above-mentioned wetting agent to render it non-adhesive to surrounding tissue. The IPN hydrogel is prepared by incorporating a second polymer network into a first hydrogel. After preparation, the IPN hydrogel is washed extensively to remove any unreacted components. To secure the hydrogel to tissue proximal the wound, the kit may further comprise one or more fasteners configured for securing the hydrogel to tissue proximal the wound, such as adhesives, sutures, tissue anchors, staples, clamps, and combinations thereof.

US 2006/015083 describes an absorbent (porous) hydrogel that is suitable for use in wound and burn dressings. The porous hydrogel, e.g. a hydrogel foam, is prepared by polymerizing a mixture comprising a hydrophilic monomer and optionally co-monomers, wherein the mixture comprises a first portion including a relatively high concentration of introduced gas bubbles and a second portion including a relatively low concentration of gas bubbles. The first portion of the mixture forms the porous portion of the hydrogel composition after polymerisation, and the second portion of the mixture forms the continuous portion of the hydrogel composition after polymerisation. The porous hydrogel can imbibe secondary components in liquid form during manufacturing. The liquid composition comprising the secondary components of the hydrogel composition is applied immediately or shortly after polymerisation (preferably on the same day) of the porous structure, and any subsequent curing, setting or drying will take place within the same say in order to increase the mechanical strength of the hydrogel material. The hydrogel material so formed can then be packed and sealed or may be further processed into a manufactured article comprising the hydrogel. It is described that, by performing the post-imbibing procedure in situ immediately or soon after the polymerisation of the porous hydrogel, the manufacturing process can be simplified and the chances of bacterial infection or dirt contamination of the hydrogel material be reduced.

US 2020/181426 describes compositions comprising a hydrogel and a liner, wherein a surface of the hydrogel dissociably-engages a surface of the liner. The compositions are provided for protecting from fouling the surfaces of a device, such as an implantable medical device or a surgical instrument, and may include a hydrophobic glue, such as commercially available superglue.

As widely accepted in the community, the main challenge towards designing a surgical adhesive or sealant is to achieve sufficient adhesion strength to the tissue, particularly in the chemically harsh environments encountered in the abdominal cavity, without negatively impacting the tissue function (Li et al., 2017, Blacklow et al., 2019; Bouten et al., 2014; Ryu et al., 2019). In consequence, there is an unmet medical need to provide suture and/or staple supports and/or sealing materials which remain stably bound to the suture site, stapled site or stoma site in chemically harsh environments, that are resistant to degradation by intestinal fluids, and, that have the capability of absorbing biological fluids.

Thus, it is an object of the present invention to mitigate at least some of these drawbacks of the state of the art. In particular, it is an aim of the present invention to provide suture and/or staple supports and/or sealing materials that strongly adhere to soft tissues, particularly in the abdominal region, and remain stably bound to a sutured/stapled site, in particular an anastomosis site, after surgery.

Further, it is an aim of the present invention to provide suture/staple supports and/or sealing materials that are resistant to degradation by biological fluids such as intestinal fluids, biliary gastric fluids and other bodily fluids.

Furthermore, it is an aim of the present invention to provide suture and/or staple supports and/or sealing materials that are capable of absorbing biological fluids.

In addition, it is an aim of the present invention to alleviate the need for artificial drains to the patient's body.

In addition, it is an aim of the present invention to mitigate the risk for septic peritonitis or other adverse events in the case of leakage of a sutured or stapled soft tissue reconnection site.

It is a further aim of the present invention to provide a process for manufacturing of patches suitable for such suture and/or staple supports and/or for such sealing.

It is a further aim of the present invention to provide a method for treating a sutured or stapled site or stoma site in a subject in need thereof.

One or more of the above objectives are achieved by a kit of parts as defined in claim 1, the manufacture of said kit of parts as defined in claim 12 and the use of an impregnating fluid as defined in claim 14. Further aspects of the invention are disclosed in the specification and independent claims, preferred embodiments are disclosed in the specification and the dependent claims.

The present invention will be described in more detail below. It is understood that the various embodiments, preferences and ranges as provided/disclosed in this specification may be combined at will. Further, depending on the specific embodiment, selected definitions, embodiments or ranges may not apply. Unless otherwise stated, the following definitions shall apply in this specification:

As used herein, the term "a", "an", "the" and similar terms used in the context of the present invention (especially in the context of the claims) are to be construed to cover both the sin-gular and plural unless otherwise indicated herein or clearly contradicted by the context.

As used herein, the terms "including", "containing" and "comprising" are used herein in their open, non-limiting sense. It is understood that the various embodiments, preferences and ranges may be combined at will.

The terms "treating", "treat" and "treatment" include one or more of the following: (i) preventing a disease, pathologic or medical condition from occurring (e.g. prophylaxis); (ii) inhibiting the disease, pathologic or medical condition or arresting its development; (iii) relieving the disease, pathologic or medical condition; (iv) diminishing symptoms associated with the disease, pathologic or medical condition; (v) monitoring the application site. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The term "surgery" is known in the field and relates to surgical procedures involving operative manual and/or instrumental techniques on a person to investigate or treat a pathological condition such as a disease or injury, to help improve bodily function or appearance or to repair unwanted ruptured areas. In specific embodiments, the term surgery relates to resection, i.e. partial removal of an organ or other bodily structure. Resection of organs such as intestines involves their reconnection. Typically, internal suturing or stapling is used for reconnection. Surgical connection between blood vessels or other tubular or hollow structures such as loops of intestine is called anastomosis. Thus, in specific embodiments, the term surgery relates to anastomosis. In some cases, surgical procedures involve creation of artificial stoma that can be temporary or permanent and sealing of such stoma. Thus, in specific embodiments, the term surgery relates to sealing of artificial stoma, particularly temporary or permanent stoma.

The term "non-degradable" as used in the context of the present invention relates to the stability of a material when in contact with biological fluids under physiological conditions. More specifically, within the scope of the present invention, a non-degradable hydrogel refers to a hydrogel of which at least 80% remains intact upon incubation for 24 h at 37° C. in bile or simulated intestinal fluid (SIF) compared to incubation in PBS.

The term "synthetic" as used in the context of the present invention relates to material which is not of biological origin, e.g. synthetic polymers. A synthetic hydrogel may comprise components that are of biological origin, however the synthetic hydrogel as such is not of biological origin.

Throughout this specification a number of abbreviations are used, including:

AA Acrylic acid
AAm acrylamide
BAC N,N'-bis(acryloyl)cystamine
CBX-SS carboxybetaine disulphide crosslinker
CMC carboxymethylcellulose
CT computer tomography
DMAEP 2,2-dimethacroyloxy-1-ethoxypropane
HSA human serum albumin
MA methyl acrylate
mBAA N,N'-Methylenebisacrylamide
mIPN mutually interpenetrating network
MPC methacryloyloxyethyl phosphorylcholine
MRI magnetic resonance imaging
NHS n-hydroxysuccinimide
NVA N-vinyl acetamide
OD optical density
PAMPS poly(2-acrylamido-2-methyl-1-propanesulfonic acid)
PBS phosphate buffered saline
PCL polycaprolactone
PEG polyethylenglycol
PEGDMA polyethylene glycol dimethacrylate
PHEMA poly(2-hydroxyethyl methacrylate)
PHPMA poly(N-(2-hydroxypropyl)methacrylamide)
PNAGA poly N-acryloyl glycinamide
PNHEA poly(N-hydroxyethylacrylamide); synonymously: poly-N-(2-hydroxyethyl)acrylamide; polyDuramide; polyHEAA
PVA polyvinylacetate
PVDF polyvinylidene difluoride
RFID radio-frequency identification
SGF simulated gastric fluid
SIF simulated intestinal fluid
TEMED N, N, N',N'-Tetramethylethan-1,2-diamin
TriMPTA 1,1,1-trimethylolpropane triacrylate
VEGF vascular endothelial growth factor
wt % weight %
vol % volume %

The present invention will be better understood by reference to the figures.

FIG. 1: Scheme illustrating kit of parts (a) and tissue treatment method (b). (a:1) Patch, (a:2) impregnating fluid, (a:2.1) monomers, (a:2.2) initiators, (a:2.3) additive 1, (a:2.4) additive 2. (a:3) inventive kit of parts. (a:(a)) Contacting patch and tissue with impregnating fluid. (b:3') Patch impregnated with fluid on tissue. (b:1) Patch, (b:2') mIPN, (b:4) soft tissue, (b:5) suture/staple site.

Figure 2:
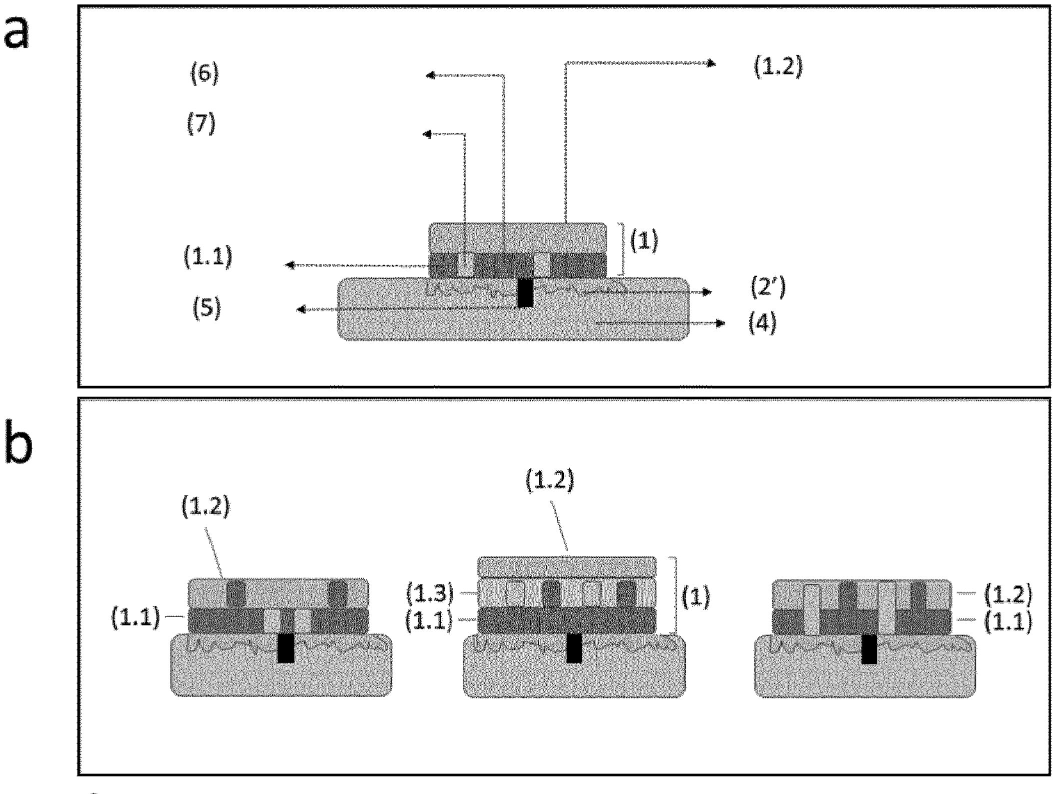

FIG. 2: Scheme illustrating cross-section of patch applied on soft tissue and different embodiments of the invention (a, b). (a:1) Patch, (a:1.1) hydrogel support layer, (a:1.2) backing layer (a:2') mIPN, (a:4) soft tissue, (a:5) Suture or stapled tissue perforation, (a:6) sensing component, (a:7) therapeutic component. (b:1.1) Hydrogel support layer. The hydrogel support layer may comprise functional components such as sensing and/or therapeutic components. (b:1.2) Backing layer. The backing layer may comprise functional components, such as sensing and/or therapeutic components. (b:1.3) Additional layer (encasing sensing and/or therapeutic matrix) comprising sensing and/or therapeutic components.

Figure 3:
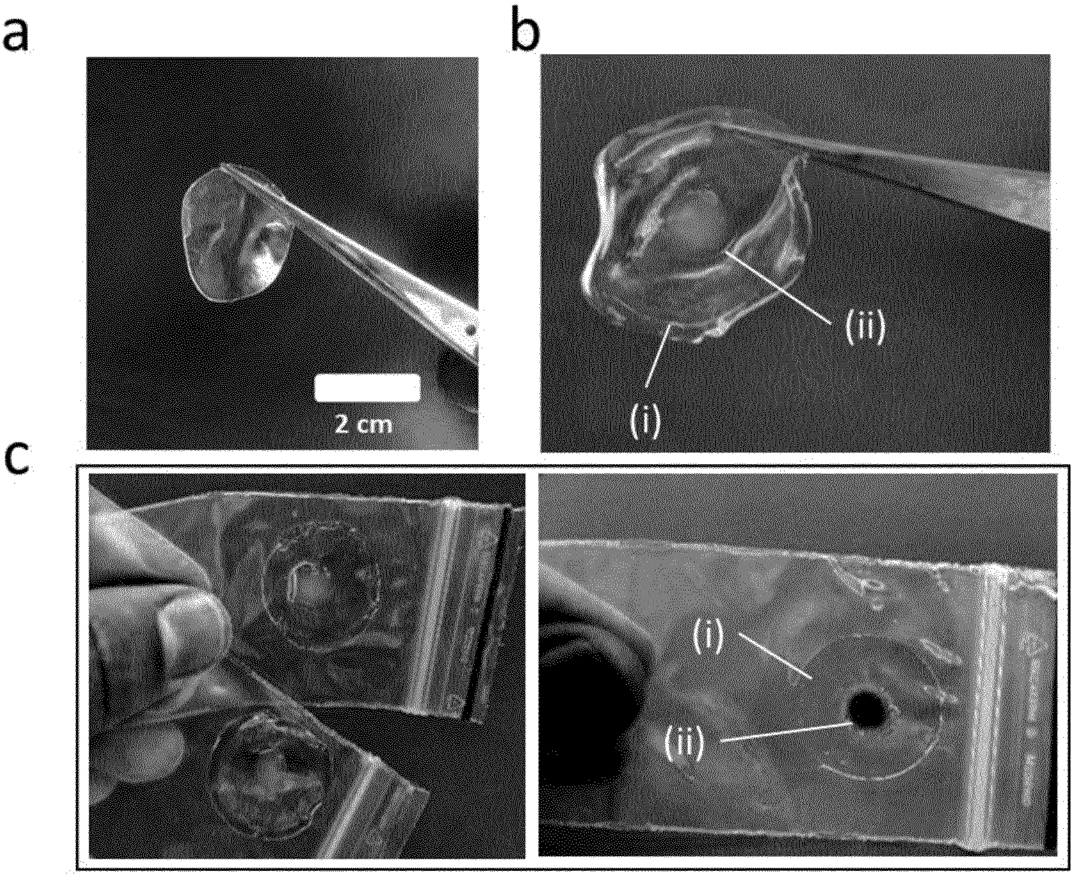

FIG. 3: Representative patches according to this invention.

(a) Patch with the shape of a disk without additional layers or functional components (example 1a, no additional layers or functional components)
(b) (i) disk shaped patch comprising (ii) ultrasound sensing component (20% vol gas-containing vesicles) and 20 wt % acrylamide, crosslinked using a 2 wt % mBAA solution (example 3a).
(c) Two disk shaped patches comprising a sensing component (left). Right: Patch comprising 20% vol gas-containing vesicles (sensing component) embedded in a crosslinked 15 wt % bovine serum albumin matrix (glutaraldehyde as crosslinker).

Figures 4, 5:
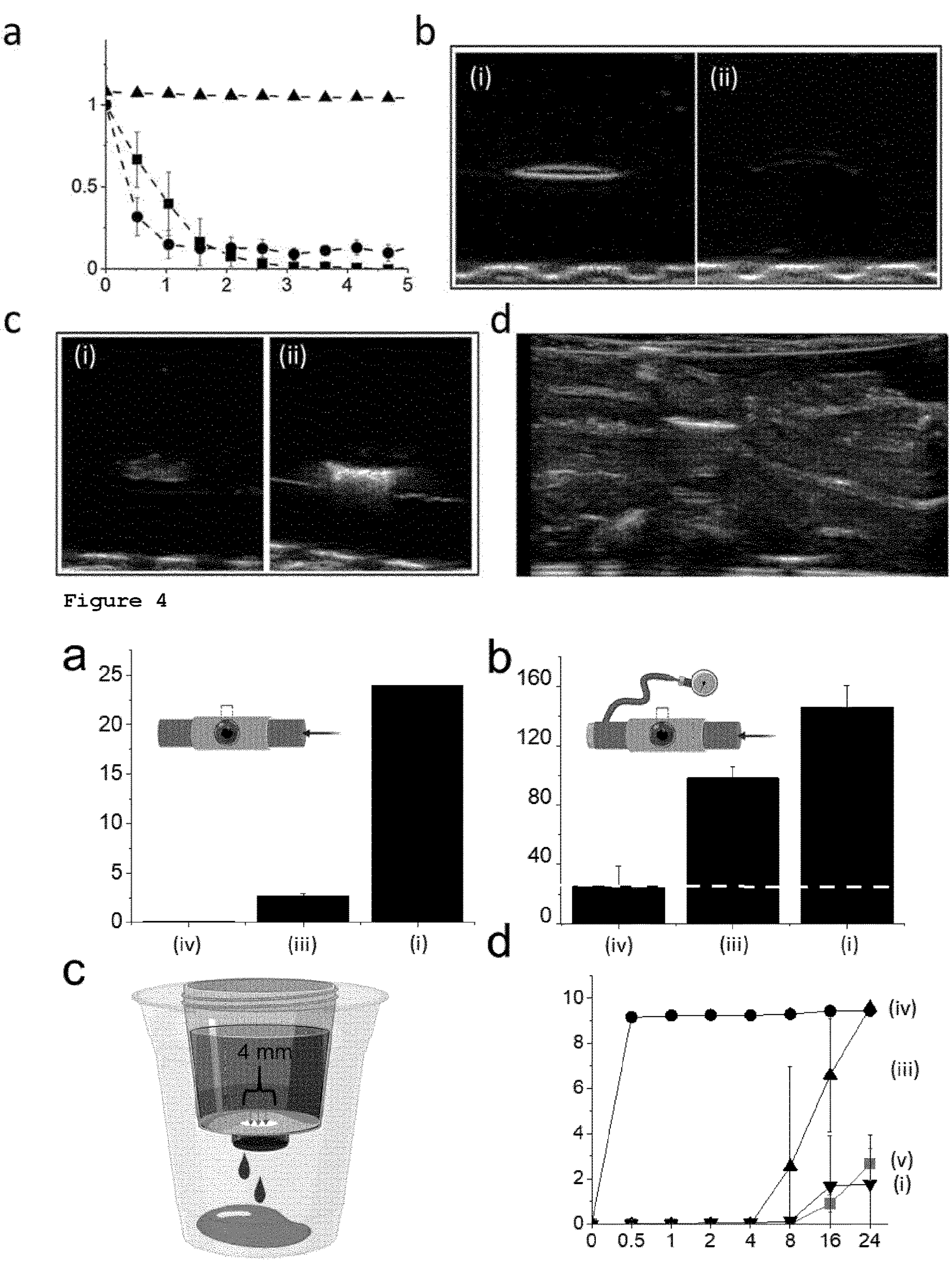

FIG. 4: (a) Normalized absorbance spectrum of a 40 vol % (squares), 20 vol % (circles) gas-containing vesicle suspension in presence of enzymatically active simulated intestinal fluid compared to enzyme deficient intestinal fluid as control (triangles), as function of time in hours. (b) Ultrasound image of "turn-off" sensing component obtained using a Clarius L15HD probe (i) before and (ii) after contact with enzyme active intestinal fluid. The sensing component is 20 vol % gas-containing vesicles embedded in 20 wt % AAm imaging phantom (black background) as described in example 3a (50 μL of mixture used for mold-curing). (c) Ultrasound image of a "turn-on" sensing component obtained using a Clarius L15HD probe (i) before and (ii) after contact with simulated gastric fluid. The sensing component is $NaHCO_3$ embedded in a hydrogel (encasing sensing matrix) comprising agar inside an AAm imaging phantom as described in example 3b. (d) Ultrasound image of a layered patch comprising a hydrogel support layer and a backing layer and a "turn-off"-type sensing component embedded in an encasing sensing matrix, attached to porcine small intestine. The hydrogel support layer comprises N-acryloyl glycinamide monomeric units (PNAGA polymer; 150 μL monomer solution used for mold-curing; rectangular shape). The backing layer comprises 20 wt % AAm monomeric units. 20% vol gas-containing vesicles are embedded in an encasing sensing matrix comprising AAm monomeric units (20 wt %). An impregnating fluid comprising N-acryloyl glycinamide curable monomers was used to generate a PNAGA mIPN that fixates the patch on the tissue. The image was obtained using a Clarius L15HD probe.

FIG. 5: (a) Ex-vivo flow model simulating the flow of intestinal fluid at 1 mL/min. Illustrated by tubular porcine intestine piece equipped with a 4 mm leaking hole. The model indicates leakage at discrete time points (y-axis) for the (iv) Tachosil surgical patch, (iii) P(AAm-AA-MA) patch (example 1a, no additional layers, mBAA crosslinked) without mIPN and (i) P(AAm-AA-MA) patch (example 1a, no additional layers, mBAA crosslinked) with an mIPN generated from an impregnating fluid comprising AAm and AA and MA and mBAA curable monomers in MilliQ water. Y-axis indicates time before leaking (hours). (b) Burst pressure measurements illustrated by a tubular porcine intestine piece equipped with a 4 mm leaking hole and an in-line manometer. Y-axis in mm Hg, burst pressure for the (iv) Tachosil surgical patch, (iii) P(AAm-AA-MA) patch (example 1a, no additional layers, mBAA crosslinked) without mIPN and (i) P(AAm-AA-MA) patch (example 1a, no additional layers, mBAA crosslinked) with an mIPN generated from an impregnating fluid comprising AAm and AA and MA and mBAA curable monomers in MilliQ water. Dashed line indicates the maximal native intestinal pressure in humans. (c) Illustration of stationary ex-vivo model simulating pooling of intestinal fluid at leakage site blocked by patch. (d) Ex-vivo stationary model results indicating leaked mass (y-axis in g) of intestinal fluid over time in hours.

i: P(AAm-AA-MA) patch (example 1a, no additional layers, mBAA crosslinked) with an mIPN generated from an impregnating fluid comprising AAm and AA and MA and mBAA curable monomers in MilliQ water;

iii: P(AAm-AA-MA) patch (example 1a, no additional layers, mBAA crosslinked) without mIPN;

iv: Tachosil surgical patch;

v: Control (tubular porcine intestine piece without hole).

Figure 6:
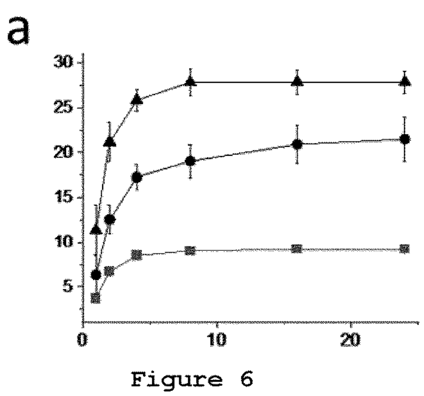
Figure 6:
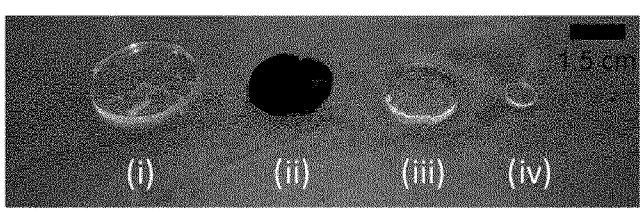

FIG. 6: Non-degradability (non-digestibility) and leak absorbing properties of P(AAm-AA-MA) patches (example 1a, no additional layers) upon incubation in biological fluids. (a) Swelling ratio defined as the mass of the patch as prepared over the mass of the incubated patch after 24 h, as a function of time in hours. PBS incubation (squares), simulated bile fluid (circles) and simulated intestinal fluid (triangles). (b) Images of P(AAm-AA-MA) patches after 24 h and 37° C. immersive incubation in (i) SIF, (ii) bile, (iii) PBS, (iv) fresh. The data show stability of the patch.

Figure 7:
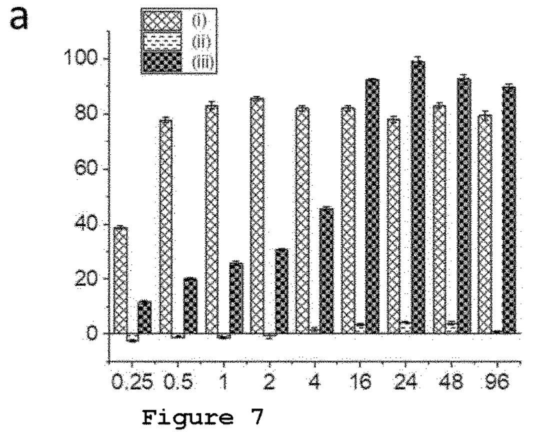
Figure 7:
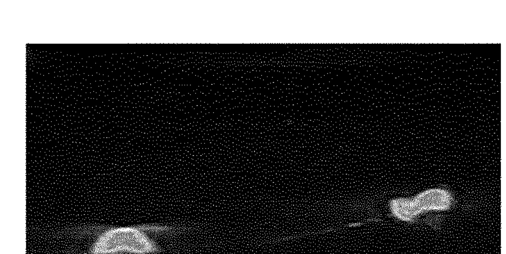

FIG. 7: Therapeutic component release and ultrasound imaging. (a) Release percentage (y-axis) as a function of time (in hours) for therapeutic components with antibacterial properties. 1 mg/mL ZnO nanoparticle were embedded in an encasing matrix comprising 20 wt % AAm (in analogy to example 4a) and incubated in (i) SIF, (ii) PBS and (iii) bacterial growth medium (tryptic soy broth). (b) Ultrasound image indicating the detectability of 10 wt % ZnO nanoparticle (2.5 mg/ml ZnO) in 20 wt % AAm encasing matrix embedded in an acrylamide imaging phantom obtained using a Clarius L15HD probe.

Figure 8:
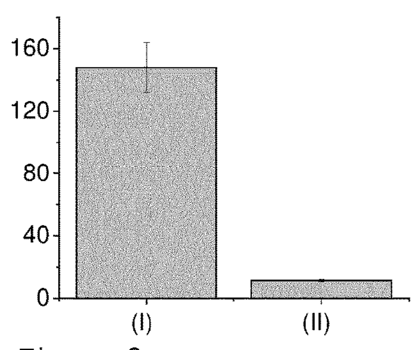

FIG. 8: Influence of impregnating fluid on adhesion strength. (i) Patch, consisting of a hydrogel support layer containing a non-degradable PAMPS hydrogel and a backing layer containing a non-adhesive PNHEA polymer was impregnated (immersed) with 3000 μL of the impregnating fluid [6 mL stock solution of the impregnating fluid contained: 2 g NAGA (N-acryloyl glycinamide), 4 mL milliQ water, 450 μL 6.33 mg/mL LAP] immediately before application on the tissue and cured after application (this invention).

(ii) Same patch as in (i) was impregnated with the impregnating fluid (same as (i)) and cured prior to application on the tissue. Y-axis: Adhesion energy (J/m^2) of the patch to porcine small intestine as measured according to ASTM standard F 2256-05 (T peel test.

This is shown in example 7.

Figure 9:
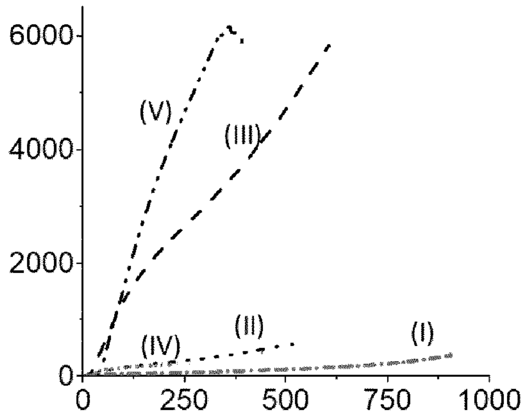

FIG. 9. Influence of backing layer and impregnating fluid on tensile strength.

Representative tensile strength curves of different patches and individual layers of the patches. (I) Hydrogel support layer containing a synthetic, non-degradable PAMPS hydrogel (no additional layers). Hydrogel support layer was prepared as described in example 1b (prepared from a polymerizable mix composed of 4 mL 50 wt % AMPS, 20 μL mBAA 2 wt %, 30.6 μL 4.825 mg/mL initiator I2959). (II) Backing layer containing PNHEA as non-adhesive polymer (no additional layers). Backing layer was prepared as described in example 2c (prepared from a polymerizable mix composed of 2 mL NHEA, 2 mL MilliQ water, 53.32 μL mBAA, 301.3 μL 4.825 mg/mL I2959). (III) PNAGA hydrogel obtained by curing an impregnating fluid with the following composition: 2 g NAGA, 4 mL milliQ water, 450 μL 6.33 mg/mL LAP). (IV) Patch consisting of hydrogel support layer and backing layer (hydrogel support layer containing PAMPS hydrogel as describe in example 1b and backing layer containing non-adhesive PNHEA polymer as described in example 2c), (V) Patch consisting of hydrogel support layer (cf. line I) and backing layer (cf. line II) after impregnation with impregnating fluid and curing of the curable monomers present in the impregnating fluid (PNAGA; cf. III). A mutually interpenetrating network is formed by curing the curable monomers present in the impregnating fluid.

Experimental details are described in example 9.

X-axis: Strain (%); Y-axis: Stress (MPa)

Figure 10:
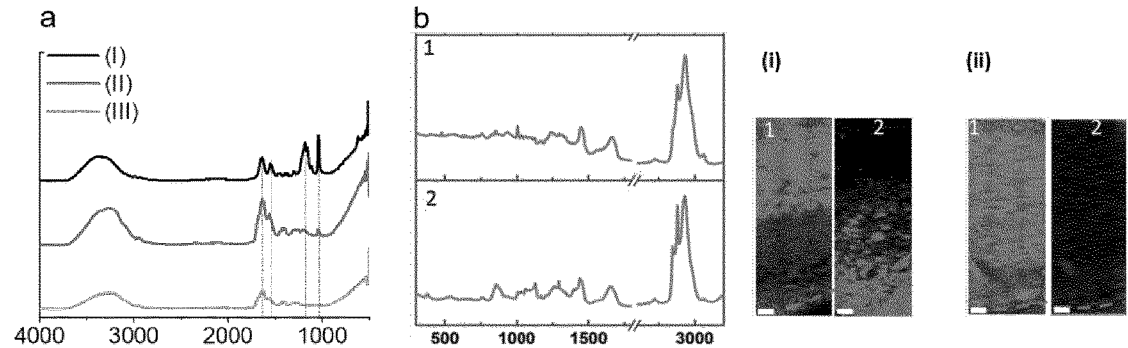

FIG. 10. Penetration of impregnating fluid into both patch and tissue after application (a) FTIR measurements indicating that the impregnating fluid (originating from a polymerizable mix composed of 33 wt % PNAGA, i.e. 2 g NAGA, 4 mL milliQ water, 450 μL 6.33 mg/mL LAP) penetrates into a patch consisting of a hydrogel support layer (containing a PAMPS hydrogel as described in example 1b). (I) Hydrogel support layer as prepared and (II) hydrogel support layer after impregnation with impregnating fluid and curing. Dotted lines indicate 1039 $cm^{-1}$ (S—O), 1183 $cm^{-1}$ (PAMPS characteristic peak), 1557 $cm^{-1}$, 1633 $cm^{-1}$ characteristic amide peaks of PNAGA (mIPN formed after curing; cf. X. Zhang, et al., J. Mater. Chem. B 2017, 5, 5588).

(b) Raman spectromicroscopy of porcine tissue serosa indicating presence of PNAGA mutually interpenetrating network in the tissue after patch application and curing (I). K-means clustering maps and spectra of histological sections of patch-sealed small porcine intestine are shown. Maps of cluster 1 (biological tissue, in bright) and cluster 2 PNAGA mIPN (polymer-rich bright) show tissue penetration of around 30 micrometer.

Raman spectromicroscopy map of native intestine before application of impregnating fluid (II), showing the tissue (cluster 1). Corresponding Raman spectra of the different clusters showing characteristic peaks for native tissue, e.g. at 1003 $cm^{-1}$, 1448 $cm^{-1}$ and 1655 $cm^{-1}$ (1) and peaks from PNAGA (2), e.g. at 860 $cm^{-1}$. Scale bars 10 micrometer.

Experimental details for both (a) and (b) are described in example 10.

Figure 11:
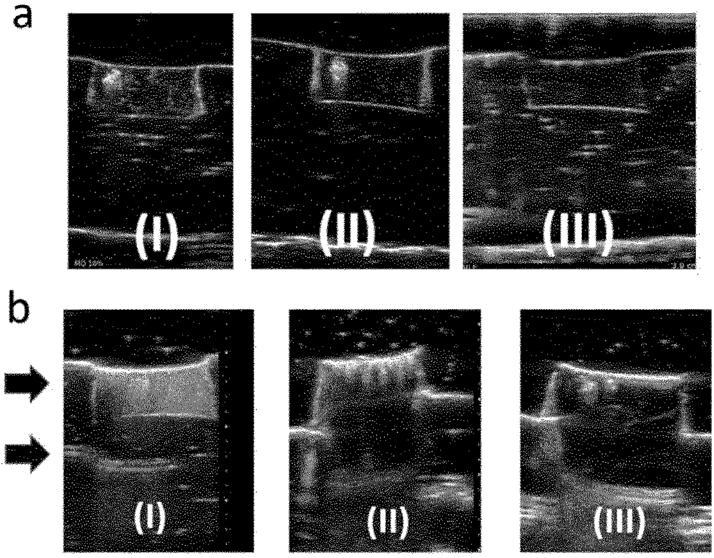

FIG. 11: Aerogel sensing component. (a) 50 μL hydrophobic alginate—sodium cholate aerogels (example 3c) incubated in different digestive effluents inside a polyacrylamide ultrasound phantom. (I) Incubated in pure water (MilliQ), (II) simulated gastric fluid, (III) following incubation in Bile or SIF full dissolution within 24 hours.

(b) Superhydrophobic Lumira silica aerogel placed inside a polyacrylamide ultrasound phantom incubated in different digestive effluents. Top arrow indicates top part of the well and aerogel particles floating. Bottom arrow indicates bottom of the well and sunk/contrast altered particles. (I) SGF (II) SIF, (III) Bile.

Ultrasound imaging was performed using a Clarius L7HD ultrasound probe controlled by an iPad. An Acrylamide hydrogel phantom served as a sample holder during ultrasound imaging. Phosphate buffered saline was used as an acoustic coupling medium.

Figure 12:
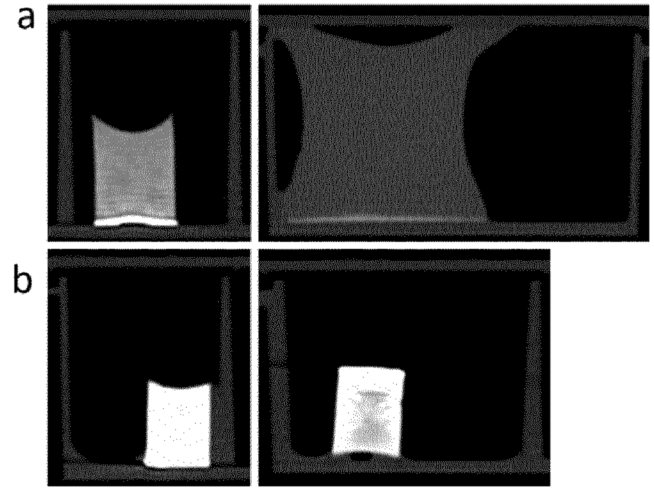

FIG. 12: X-ray CT sensing components.

(a) (Left): poly(2-acrylamido-2-methyl-1-propanesulfonic acid) (PAMPS) containing 5 wt. % tantalum oxide before exposure to SIF (example 3e).

(Right): PAMPS containing 5 wt. % tantalum oxide after exposure to SIF (example 3f).

(b) (Left): PNAGA containing 10 wt. % tantalum oxide before SIF exposure.

(Right): PNAGA containing 10 wt. % tantalum oxide after SIF exposure.

CT imaging was performed under a constant angle acquisition using a single X-Ray source and a KVP of 120 kV. Images were reconstructed using a UR77 kernal.

Figure 13:
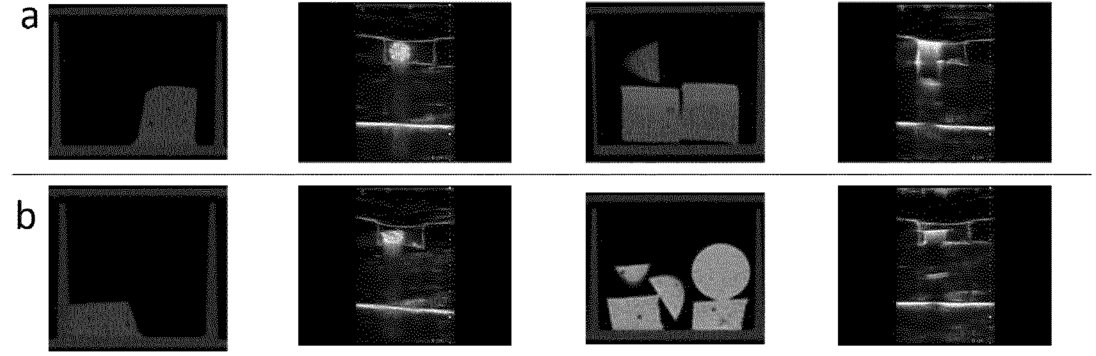

FIG. 13: Dual contrast sensing components. (a) CT and ultrasound images of 2 wt. % Agar containing 35 wt. % NaHCO3 (example 3b).

(Two images on the left): CT and ultrasound image after SGF (+10% HCl) exposure. Resulting bubble structure is visible under CT and ultrasound.

(Two images on the right): CT and ultrasound image before SGF exposure.

b) CT and ultrasound images of 2 wt. % Agar containing 35 wt. % CaCO3 (example 3g)

(Two images on the left): CT and ultrasound image after SGF (+10% HCl) exposure. C02 bubbles are visible in ultrasound and a decreased contrast is seen in CT.

(Two images on the right): CT and ultrasound image of gels before SGF exposure. Few bubbles from Agar fabrication are visible under CT.

Ultrasound imaging was performed using a Clarius L7HD ultrasound probe controlled by an iPad. An Acrylamide hydrogel phantom served as a sample holder during ultrasound imaging. Phosphate buffered saline was used as an acoustic coupling medium. CT imaging was performed under a constant angle acquisition using a single X-Ray source and a KVP of 120 kV. Images were reconstructed using a UR77 kernal.

Figure 14:
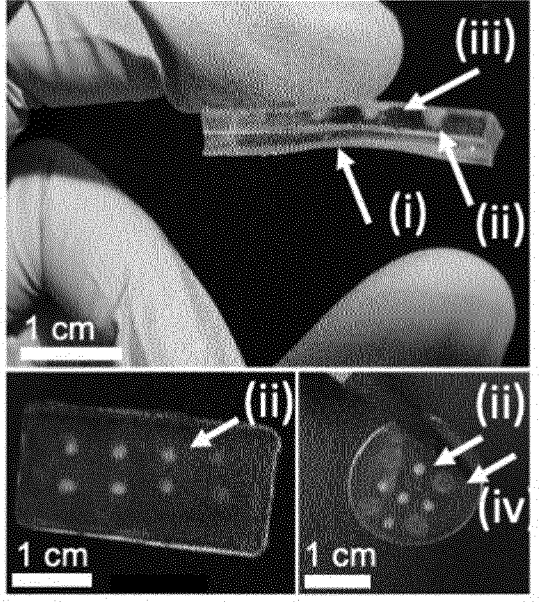

FIG. 14: Top, bottom left: Rectangular layered patch consisting of (i) backing layer containing PNHEA 50 wt %, (ii) 20 wt % Halo gas vesicle (sensing component) embedded in PAAm, inside (iii) hydrogel support layer (50 wt % PAMPS).

Bottom right: Layered circular patch comprising (i)-(iii) as in the top and bottom left gels additionally containing (iv) 2.5 wt % ZnO (therapeutic component).

Figure 15:
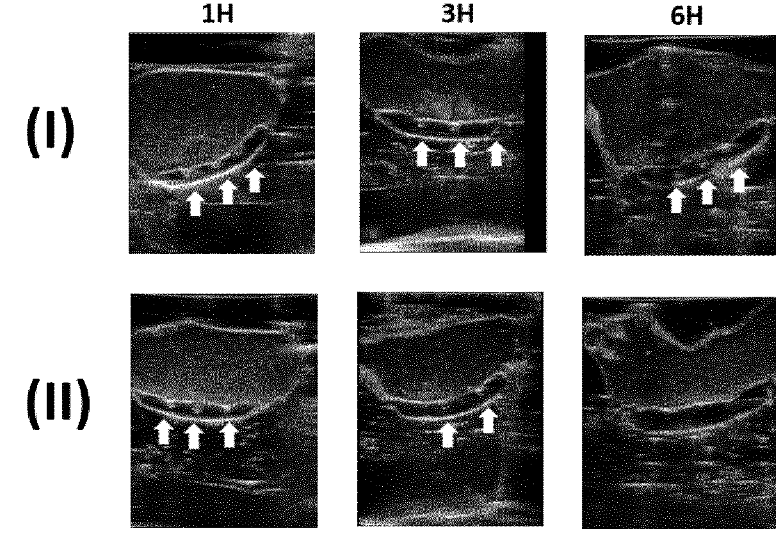

FIG. 15: Ultrasound images performed using a Clarius 7HD probe controlled by an Ipad, performed at discrete time intervals (1, 3 and 6 hours) of a circular layered patch containing gas-containing vesicles as sensing component (patterned circular sensing patch). The patch covered an intestine filled with simulated microbially active and enzyme rich digestive fluid. The patch contained a hydrogel support layer comprising a 50 wt % PAMPS hydrogel and a PAAm hydrogel embedded in the hydrogel support layer, wherein gas-containing vesicles are embedded in the PAAm hydrogel (period arrangement of 5 μL of 20 vol % gas-containing vesicles in PAAm matrix), and a backing layer containing PNHEA. The patch was attached to the tissue wall using an impregnating fluid containing 33 wt % NAGA and a 5 min UV light polymerization step. Condition (I) refers to the absence of a perforation on the tissue wall and (II) to the presence of a perforation at the site of the patch. Loss of contrast can be observed in (II) as a consequence of gastrointestinal fluid contact with the sensing components, indicating the leak and resulting from the firm attachment of the patch to the tissue wall. In absence of a leak, contrast remains unchanged.

Figure 16:
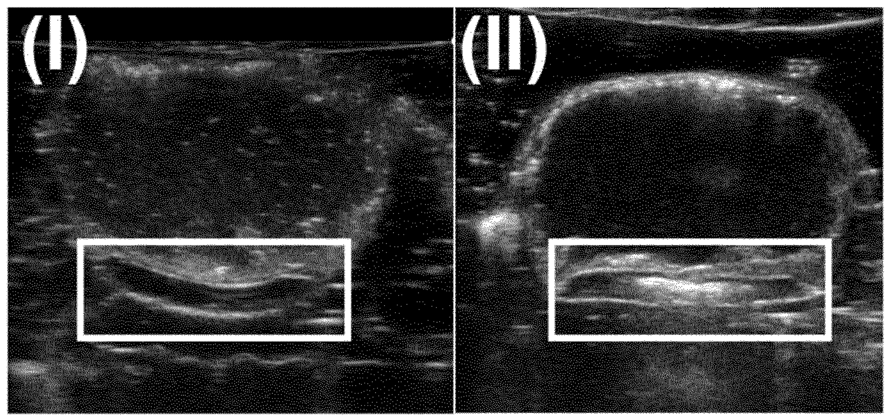

FIG. 16: Ultrasound images of patches detecting a digestive leak. (a) Disk shaped patch containing a 50 wt % PAMPS hydrogel support layer, and 2 wt % NaHCO3 (sensing component) embedded in 2 wt % agar. The patch was attached to the tissue wall using an impregnating fluid containing 33 wt % NAGA and a 5 min UV light polymerization step. Condition (I) the patch is attached to a porcine intestinal tissue containing SGF (simulated gastric fluid pH=2) but the system contains no perforation. (II) the system is perforated at the level of the patch, inducing pro-duction of CO2 within the patch and a change in observable contrast (in 15 min post contact).

In more general terms, in a first aspect, the invention relates to a kit of parts comprising a first part and a second part, wherein the first part is a shaped article in the form of a patch, the patch comprising a hydrogel support layer, optionally a backing layer and optionally functional components selected from sensing components or therapeutic components. The hydrogel support layer comprises a non-degradable, synthetic hydrogel. The optional backing layer comprises a non-adhesive polymer. The second part is an impregnating fluid comprising a pharmaceutically acceptable liquid, and curable monomers, and optionally curing initiators, and optionally additives.

The impregnating fluid is adapted to penetrate into the shaped article (patch) and a tissue. The impregnating fluid is provided as a separate component of the kit. The kit of parts is ready for use in a surgical method. Both the shaped article and the impregnating fluid are suitable for application on a sutured site, a stapled site or a stoma site of a subject in need thereof.

The patch and the impregnating fluid are each separately packed for transport and/or sale. The patch and the impregnating fluid are each separately packed prior to the use in a surgical method. As used herein, the term "separately packed" also includes "packed in one packaging, such as a pouch, wherein the patch and the impregnating fluid are present in two separate compartments of the same packaging. Such compartments may be separated by a removable barrier element. Removal of the barrier element, if it is present, allows impregnation of the patch with the impregnating fluid.

The patch is impregnated with the fluid shortly before application on a tissue. Curing of monomers that are present in the impregnating fluid is initiated after application of the impregnated patch on a tissue. Thus, in a non-applied state the monomers present in the impregnating fluid are not cured (monomeric state). In an applied state (application of the impregnated patch on a tissue), the monomers are cured (polymeric state). The pharmaceutically acceptable liquid is selected from water and/or glycerol.

The optional curing initiator is adapted for curing the curable monomers. Selecting a suitable curing initiator is within the ordinary skill.

Such kit of parts may be manufactured as described below and applied to a subject in need thereof as described below. When applied to soft tissue, the patches are suited as suture and staple supports and/or sealing materials that adhere to such soft tissue, particularly in the abdominal region, and remain stably bound to a sutured or stapled site, in particular an anastomosis site, after surgery.

While the patch provides, as a main function, sealing properties, the impregnating fluid provides, as a main function, gluing properties. The function of the patch may be enhanced by including functional components that allow monitoring of the application site and/or preventing adverse events after leakage of a sutured/stapled site or that improve wound healing.

This aspect of the invention, particularly materials suitable for the kit of parts, are described in further detail below and illustrated in FIGS. 1 and 2.

Hydrogel Support Layer:

The hydrogel support layer comprises a non-degradable synthetic hydrogel. The main function of the hydrogel support layer is to provide sealing properties to support a sutured site, a stapled or a stoma site. The hydrogel support layer may also be referred to as a suture support layer. Hydrogels are known per se. Typically, a hydrogel is a network of crosslinked polymer chains that are hydrophilic and can thus bind aqueous fluids. They are mainly identified by the monomeric units forming the polymer that in turn can form a hydrogel upon contact with a fluid. Typically, the above fluid is an aqueous fluid, e.g. water.

Although the monomeric units are no longer present in the hydrogel so formed, it is convenient in the field to still refer to the chemical class of monomeric units forming such polymer. A broad range of hydrogel forming monomeric units is known. The skilled person is in a position to select monomeric units com-patible with the field of surgery.

In a preferred embodiment, the hydrogel support layer comprises a synthetic, non-degradable hydrogel comprising one or more monomeric units selected from the group consisting of methacrylates, acrylates, vinyls, thiols, polyurethane forming monomers and mixtures thereof.

In a more preferred embodiment, the hydrogel support layer comprises a synthetic, non-degradable hydrogel comprising one or more monomeric units selected from the group consisting of methacrylates, acrylates, vinyls, and thiols.

In embodiments, the hydrogel support layer further comprises one or more pre-made synthetic polymers and/or natural polymers and/or acrylated natural polymers. Such additional polymers may be added to fine-tune the properties of the hydrogel support layer such as stability or compatibility with tissue, e.g. by maintaining mechanical stiffness over time.

Suitable methacrylates may be selected from the group consisting of methacrylic acid (MA), methyl methacrylate, methacrylamide, hydroxyethylmethacrylate, ethyl hexyl (meth)acrylate, glycidyl methacrylate, oligoethylene-glycol methylacrylate, 2-(dimethyl-amino)ethyl methacrylate, [2-(methacryloyloxy)ethyl]trimethylammonium chloride, N-(2-hydroxypropyl) methacrylamide, methacrylic anhydride, N,N-diethylmethacrylamide, (hydroxy-phenyl)methacrylamide, 2-hydroxypropyl methacrylamide, 2-ami-noethylmethacrylamide hydrochloride, methacryloyl-L-Lysine, phosphoric acid 2-hydroxyethyl acrylate ester, 4-methacryloxyethyl trimellitic anhydride, 3-sulfopropyldimethyl-3-methac-rylamidopropylammonium, methacryloyloxyethyl phosphorylcholine (MPC), 2-N-morpholinoethyl methacrylate, 2-aminoethyl methacrylate hydrochloride, methacryloyl-L-lysine, pyridyl disulfide ethyl methacrylate, N-(3-aminopropyl)methacrylamide hydrochloride, N-(3-BOC-aminopropyl)methacrylamide, O-nitrobenzyl methacrylate, O-nitrobenzyl ethyl methacrylate. It is also envisaged to use combinations of two or more methacrylates.

Preferably, methacrylates are selected from the group consisting of methacrylic acid, methyl (methacrylate), methacrylamide, hydroxyethylmethacrylate, ethyl hexyl (meth) acrylate, glycidyl methacrylate, oligoethylene-glycol methylacrylate, 2-(dimethyl-amino)ethyl methacrylate, [2-(methacryloyloxy)ethyl]trimethylammonium chloride, N-(2-hydroxypropyl) methacrylamide, methacrylic anhydride, N,N-diethylmethacrylamide, 2-hydroxypropyl methacrylamide, methacryloyloxyethyl phosphorylcholine (MPC), 2-aminoethyl methacrylate hydrochloride, pyridyl disulfide ethyl methacrylate, O-nitrobenzyl methacrylate and O-nitrobenzyl ethyl methacrylate and mixtures thereof.

Suitable acrylates may be selected from the group consisting of acrylic acid (AA), acrylamide (AAm), hydroxyethylacrylate, ethyl hexyl acrylate, butyl acrylate, 2-(dimethylamino)ethyl acrylate, (acrylamidopropyl) trimethylammonium chloride, N-(2-hydroxypropyl) acrylamide, N-acryloyl glycinamide, acrylated adenine, acrylated thymine, acrylated cytosine, acrylated guanine, acrylated uracyl, NHS acrylate, NHS sulfo acrylate, acrylic anhydride, 2-acrylamido-2-methyl-1-propanesulfonic, N,N-diethylacrylamide, (hydroxyphenyl)acrylamide, 2-hydroxypropyl acrylamide, N-isopropylacrylamide, beta-carboxyethyl acrylate, 2-N-morpholinoethyl acrylate, 2-aminoethyl acrylate hydrochloride, N-[3-(N,N-dimethylamino)propyl]acrylamide, 2-acryloxyethyltrimethylammonium chloride, 2-cyanoethyl acrylate, N-acryloxysuccinimide, 0-nitrobenzyl acrylate, 0-nitrobenzyl ethyl acrylate. It is also envisaged to use combinations of two or more acrylates.

Preferably, acrylates are selected from the group consisting of acrylic acid, acrylamide, hydroxyethylacrylate, ethyl hexyl acrylate, butyl acrylate, 2-(dimethylamino)ethyl acrylate, (acrylamidopropyl)trimethylammonium chloride, N-(2-hydroxypropyl) acrylamide, N-acryloyl glycinamide, NHS acrylate, NHS sulfo acrylate, acrylic anhydride, N,N-diethylacrylamide, (hydroxy-phenyl)acrylamide, 2-hydroxypropyl acrylamide, N-isopropylacrylamide, beta-carboxyethyl acrylate, 2-aminoethyl acrylate hydrochloride, N-[3-(N,N-dimethylamino)propyl]acrylamide, 2-acryloxyethyltrimethylammonium chloride, 2-cyanoethyl acrylate, N-acryloxysuccinimide, 0-nitrobenzyl acrylate, and O-nitrobenzyl ethyl acrylate, and mixtures thereof.

Suitable vinyls may be selected from the group consisting of vinyl pyrrolidinone, vinylcaprolactam, sodium styrene sulfonate, 2-methylene-1,3-dioxepane, 3-(acrylamido)phenylboronic acid, allyl methyl sulfone, 3-allyloxy-2-hydroxy-1-propanesulfonic acid sodium salt, 3-allyloxy-1,2-propanediol, N-methyl-N-vinyl acetamide, N-vinyl acetamide (NVA), vinylphosphonic acid, allylphosphonic acid monoammonium salt, mutliarm PEG (2 or 3 or 4 arms) vinyl sulfone. It is also envisaged to use combinations of two or more vinyls.

Preferably, vinyls are selected from the group consisting of vinyl pyrrolidinone, vinylcaprolactam, and sodium styrene sulfonate, and mixtures thereof.

Suitable thiols may be selected from the group consisting of 1,4-butanedithiol, 1,3-propanedithiol, 1,2-ethanedithiol, 2,2'(ethylenedioxy)diethanethiol, ethylene glycol bis-mercapto-acetate, 2-arm PEG-SH, 3-arm PEG-SH, 4-arm PEG-SH. It is also envisaged to use combinations of two or more thiols.

Preferably, thiols are selected from 1,3-propanedithiol and 2,2'(ethylenedioxy)diethanethiol, and mixtures thereof.

Polyurethanes are formed by reactions of polyols and isocya-nates. Suitable urethane forming monomers may be selected from the lists below. Again, two or more polyols and two or more isocyanates may be used to form the hydrogel.

Polyols: 2,4,6-Tria-mino-1,3,5-triazine, 3,5-dimethoxy-4-hydroxybenzaldehyde, polyethylene glycol (PEG 400, 600, 1000), 1,4-butanediol, CAPA™3050.

Isocyanates: Hexamethylene diisocyanate, sophoronediisocyanat, L-lysine ethyl ester diisocyanate, isophorone diisocyanate.

Suitable natural polymers may be selected from the group consisting of alginate, chitosan, carboxymethylcellulose, dextran, heparin, hyaluronic acid, gellan gum, and kappacarraggennans.

Suitable acrylated natural polymers may be selected from the group consisting of acrylated elastin, acrylated albumin, acrylated alginate and acrylated human serum albumin.

Suitable pre-made synthetic polymers may be selected from the group consisting of polyacrylic acid, poly(N-(2-hydroxypropyl)methacrylamide) (PHPMA), polyvinylacetate (PVA), polycapro-lactone (PCL), poly(2-hydroxyethyl methacrylate) (PHEMA), polyvinylidene difluoride (PVDF), polyethylene glycol (PEG 400, 600, 1000), polydopamine, polygallic acid, hydroxyethylmethacrylate.

Preferably, pre-made synthetic polymers are selected from the group consisting of polyacrylic acid, PHPMA, PVA, PHEMA, PVDF, polyethylene glycol (PEG 400, 600, 1000), polydopamine, and polygallic acid.

Typically, one or more monomeric units comprised within said non-degradable, synthetic hydrogel function as crosslinkers. Such crosslinkers are known in the field and selected in accordance with the monomer units of the hydrogel.

Some monomers, particularly monomers that have relatively strong H-bond interactions such as N-acryloyl glycinamide (NAGA) do not require the addition of crosslinkers to form a hydrogel. However, most monomers require addition of crosslinkers to form a hydrogel.

As convenient in the field, polymers may comprise different classes of monomers as mentioned above, e.g. copolymers of acrylates and methacrylates.

Suitable crosslinkers may be selected from the group consisting of polyethylene glycol dimethacrylate (particularly PEGDMA 20000), 1,6-hexanediol diacrylate, 1,4-butanediol diacrylate, 1,4-phenylene diacrylate, bis(2-methacryloxyethyl) phosphate, triethylene glycol diacrylate (TriEGDA), dipentaerythritol pentaacrylate, 1,1,1-trimethylolpropane triacrylate (TriMPTA), 1,1,1-trimethylolpropane trimethacrylate, PEO(5800)-b-PPO(3000)-b-PEO (5800) dimethacrylate, pentaerythritol triacrylate, pentaerythritol tetraacrylate, tricyclodecane dimethanol diacrylate, PEGDA-PEG diacrylate, zinc dimethacrylate, carboxybetaine disulfide cross-linker (CBX-SS), oxidized alginate, diselenide crosslinker, 2,2-dimethacroyloxy-1-ethoxypropane (DMAEP), N,N'-bis(acryloyl)cystamine (BAC), methylene bis-acrylamide (mBAA), 1,3,5-triallyl-1,3,5-triazine-2,4,6(1H,3H,5H)-trione, mutliarm PEG (2,3,4) thiol terminated, multiarm PEG (2 or 3 or 4 arms) vinyl sulfone terminated, mul-tiarm PEG (2,3,4) NHS terminated, multiarm PEG (2 or 3 or 4 arms) NH2 terminated, 2,4,6-tria-mino-1,3,5-triazine, 3,5-di-methoxy-4-hydroxybenzaldehyde, polyethylene glycol (PEG 400, 600, 1000).

Preferably, crosslinkers are selected from the group consisting of polyethylene glycol dimethacrylate (PEGDMA 20000), 1,4-butanediol diacrylate, pentaerythritol triacrylate, PEGDA-PEG di-acrylate, zinc dimethacrylate, carboxybetaine disulfide cross-linker (CBX-SS), oxidized alginate, 2,2-dimethacroyloxy-1-ethoxypropane (DMAEP), N,N'-Bis(acryloyl)cystamine (BAC), meth-ylene bis-acrylamide, multiarm PEG (2 or 3 or 4 arms) vinyl sulfone terminated, and multiarm PEG (2 or 3 or 4 arms) NHS terminated, and mixtures thereof.

In a particularly preferred embodiment, the hydrogel support layer comprises a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris(hydroxymethyl)methyl acrylamide, bis-acrylamide, poly eth-ylene glycol diacrylate, N,N'-bis(acryloyl) cystamine, and mixtures thereof.

In a further particularly preferred embodiment, the hydrogel support layer comprises a non-degradable, synthetic poly(AAm-AA-MA) hydrogel (p (AAm-AA-MA)), comprising AAm and AA and MA and mBAA monomeric units, wherein mBAA functions as a crosslinker. This embodiment is described in example 1 and shown in FIG. 3 (*a*), FIG. 5 and FIG. 6.

In another preferred embodiment, the hydrogel support layer comprises a non-degradable, synthetic poly(2-acrylamido-2-methyl-1-propanesulfonic acid) hydrogel (PAMPS). A hydrogel support layer comprising a PAMPS hydrogel is described in example 5l.

Typically, the hydrogel support layer comprises 10-90% water. Preferably, the hydrogel support layer comprises 30-80% water, more preferably, 40-60% water, such as 40%, 45%, 50%, 55% or 60% water.

Backing Layer:

As discussed herein, the backing layer is optional. In a preferred embodiment, the patch comprises a backing layer, said backing layer comprising a non-adhesive polymer. Again, backing layers are known per se. They are included to provide structural integrity (cf. FIG. 9) and/or additional functionality as described below. Suitable backing layers can generally be prepared from the same materials as described for the hydrogel support layer, including natural polymers and/or acrylated natural polymers as described for hydrogel support layers. However, the specific composition of the backing layer in each case differs from the hydrogel support layer.

The skilled person understands that the backing layer, if present, cannot be peeled off from the hydrogel support layer. This is in contrast to a release liner which dissociably-engages the surface of a hydrogel.

The skilled person is capable of selecting a backing layer comprising a non-adhesive polymer using the above materials, including the monomeric units in a suitable ratio and/or natural polymers and/or acrylated natural polymers.

Said non-adhesive polymer can be a non-adhesive synthetic polymer comprising monomeric units selected from the group consisting of methacrylates, acrylates, vinyls, thiols, polyurethane forming monomers, and mixtures thereof in a suitable ratio and/or a suitable natural polymer and/or acrylated natural polymer. In particular, non-adhesive properties can be conferred on the backing layer by including carboxymethylcellulose (CMC), poly(N-acryloyl glycinamide) (PNAGA), poly(hydroxyethyl acrylate) (PHEA), poly(N-(2-hydroxyethyl)acrylamide) (PNHEAA).

Preferably, monomeric units comprised within said non-adhesive synthetic polymer are selected from the group consisting of methacrylates, acrylates, vinyls, thiols, and mixtures thereof.

In a preferred embodiment, the non-adhesive polymer comprised by the backing layer is poly(N-hydroxyethylacrylamide) (PNHEA). In another preferred embodiment, the non-adhesive polymer is polyurethane, more preferably a hydrophilic polyurethane such as HydroMed D4 polyurethane.

Typically, the backing layer comprises 2%-90% water. Preferably, the backing layer comprises 5%-80% water, more preferably, 5%-60% water, such as 5%, 10%, 15%, 20%, 25%, 30%, 35%, 40%, 45%, 50%, 55% or 60% water.

Impregnating Fluid

The impregnating fluid comprises a pharmaceutically acceptable liquid, curable monomers, optionally curing initiators, and op-tionally additives.

The pharmaceutically acceptable liquid is selected from water and/or glycerol.

In a preferred embodiment, the impregnating fluid comprises 10%-95% water, preferably 40%-80% water, more preferably 55%-75% water, such as 55%, 60%, 62%, 65%, 67%, 70% or 75% water.

In a preferred embodiment, the impregnating fluid comprises N-acryloyl glycinamide as curable monomers.

In a preferred embodiment, the impregnating fluid comprises a visible light photoinitiator, in particular Lithium-phenyl-2,4,6-trimethylbenzoylphosphinate (LAP).

Curable Monomers:

Curable monomers are known per se. As discussed above, the main function of the impregnating fluid is to provide gluing properties. This is achieved by penetration of the curable monomers comprised within the impregnating fluid into the patch and the tissue, thus forming a mutually interpenetrating network (mIPN) spanning both, tissue and patch, to thereby fixate the patch on the tissue. A broad range of curable monomers is known. The skilled person is in a position to select curable monomers com-patible with the field of surgery, in particular for suture supports, staple supports and/or sealants for artificial stoma, more particularly for intestinal anastomosis, stomach resection, gallbladder anastomosis, gallbladder resection, liver resection, colon resection, colon anastomosis, pancreas resection, pancreas anastomosis, portacaval anastomosis and/or a temporary stoma and/or a permanent stoma.

In general, monomeric units, including crosslinkers, that are suitable to form the synthetic polymer comprised within the hydrogel support layer are also suitable curable monomers com-prised within the impregnating fluid, e.g. methacrylates, acrylates, vinyls, thiols, and mixtures thereof.

Preferably, curable monomers comprised within the impregnating fluid are selected from the group consisting of acrylates, vi-nyls, and mixtures thereof, more preferably acrylates.

Preferably, methacrylates are selected from the group consisting of methacrylic acid, methyl (methacrylate), methacrylamide, hydroxyethylmethacrylate, ethyl hexyl (meth) acrylate, glycidyl methacrylate, oligoethylene-glycol methylacrylate, 2-(dimethyl-amino)ethyl methacrylate, [2-(methacryloyloxy)ethyl]trimethylammonium chloride, N-(2-hydroxypropyl) methacrylamide, methacrylic anhydride, N,N-diethylmethacrylamide, (hydroxy-phenyl)methacrylamide, 2-hydroxypropyl methacrylamide, 2-ami-noethylmethacrylamide hydrochloride, methacryloyl-L-lysine, phosphoric acid 2-hydroxyethyl acrylate ester, 4-methacryloxyethyl trimellitic anhydride, 3-sulfopropyldimethyl-3-methacrylamidopropylammonium, methacryloyloxyethyl phosphorylcholine (MPC), 2-N-morpholinoethyl methacrylate, 2-aminoethyl methacrylate hydrochloride, methacryloyl-L-lysine, pyridyl disulfide ethyl methacrylate, N-(3-aminopropyl)methacrylamide hydrochloride, N-(3-BOC-aminopropyl)methacrylamide and mixtures thereof. More preferably, methacrylates are selected from glycidyl methacrylate, oligoethylene-glycol methylacrylate, and mixtures thereof.

Preferably, acrylates are selected from the group consisting of acrylic acid, acrylamide, hydroxyethylacrylate, ethyl hexyl acrylate, butyl acrylate, 2-(dimethylamino)ethyl acrylate, (acrylamidopropyl)trimethylammonium chloride, N-(2-hydroxypropyl) acrylamide, N-acryloyl glycinamide, acrylated adenine, acrylated thymine, acrylated cytosine, acrylated guanine, acrylated uracyl, NHS acrylate, NHS sulfo acrylate, acrylic anhy-dride, 2-acrylamido-2-methyl-1-propanesulfonic, N,N-diethylacrylamide, (hydroxyphenyl)acrylamide, 2-hydroxypropyl acrylamide, N-isopropylacrylamide, beta-carboxyethyl acrylate, 2-N-morpholinoethyl acrylate, 2-aminoethyl acrylate hydrochloride, N-[3-(N,N-dimethylamino)propyl]acrylamide, 2-acryloxyethyltrimethylammonium chloride, 2-cyanoethyl acrylate, N-acryloxysuccinimide, and mixtures thereof.

More preferably, acrylates are selected from the group consisting of acrylic acid, acrylamide, hydroxyethylacrylate, ethyl hexyl acrylate, butyl acrylate, 2-(dimethylamino)ethyl acrylate, (acrylamidopropyl)trimethylammonium chloride, N-(2-hydroxypropyl) acrylamide, N-acryloyl glycinamide, acrylated adenine, acrylated thymine, acrylated cytosine, acrylated guanine, acrylated uracyl, NHS acrylate, NHS sulfo acrylate, acrylic anhydride, 2-acrylamido-2-methyl-1-propanesulfonic, N,N-diethylacrylamide, (hydroxyphenyl) acrylamide, 2-hydroxypropyl acrylamide, N-isopropylacrylamide, beta-carboxyethyl acrylate, 2-N-morpholinoethyl acrylate, 2-aminoethyl acrylate hydrochloride, N-[3-(N,N-dimethylamino)propyl]acrylamide, 2-acryloxyethyltrimethylammonium chloride, N-acryloxysuccinimide, and mixtures thereof.

Preferably, vinyls are selected from the group consisting of vinyl pyrrolidinone, vinylcaprolactam, sodium styrene sulfonate, 2-methylene-1,3-dioxepane, 3-(acrylamido)phenylboronic acid, allyl methyl sulfone, 3-allyloxy-2-hydroxy-1-propanesulfonic acid sodium salt, 3-allyloxy-1,2-propanediol, N-methyl-N-vinyl acetamide, N-vinyl acetamide (NVA), vinylphosphonic acid, allylphosphonic acid monoammonium salt, mutliarm PEG (2 or 3 or 4 arms) vinyl sulfone and mixtures thereof.

More preferably, vinyls are selected from the group consisting of vinyl pyrrolidinone, vinylcaprolactam, sodium styrene sulfonate, 2-methylene-1,3-dioxepane, 3-(acrylamido)phenylboronic acid, allyl methyl sulfone, 3-allyloxy-2-hydroxy-1-propanesulfonic acid sodium salt, 3-allyloxy-1,2-propanediol, N-methyl-N-vinyl acetamide, N-vinyl acetamide (NVA), vinylphosphonic acid, allylphosphonic acid monoammonium salt, and mixtures thereof.

Preferably, thiols are selected from the group consisting of 1,4-butanedithiol, 1,3-propanedithiol, 1,2-ethanedithiol, 2,2'-(ethylenedioxy)diethanethiol, ethylene glycol bis-mercaptoace-tate, 2-arm PEG-SH, 3-arm PEG-SH, 4-arm PEG-SH and mixtures thereof.

Typically, one or more monomeric units comprised within said impregnating fluid function as crosslinkers. Some monomers, par-ticularly monomers that have relatively strong H-bond interac-tions such as N-acryloyl glycinamide (NAGA) do not require the addition of crosslinkers to form a hydrogel. However, most monomers require addition of crosslinkers to form a hydrogel.

Preferably, crosslinkers are selected from the group consisting of polyethylene glycol dimethacrylate (PEGDMA 20000), 1,4-butanediol diacrylate, pentaerythritol triacrylate, PEGDA-PEG di-acrylate, zinc dimethacrylate, carboxybetaine disulfide cross-linker (CBX-SS), oxidized alginate, 2,2-dimethacroyloxy-1-ethoxypropane (DMAEP), N,N'-bis(acryloyl)cystamine (BAC), meth-ylene bis-acrylamide (mBAA), multiarm PEG (2 or 3 or 4 arms) vinyl sulfone terminated, multiarm PEG (2 or 3 or 4 arms) NHS terminated, and mixtures thereof.

More preferably, crosslinkers are selected from the group consisting of polyethylene glycol dimethacrylate (PEGDMA 20000), PEO(5800)-b-PPO(3000)-b-PEO(5800) dimethacrylate, PEGDA-PEG di-acrylate, carboxybetaine disulfide cross-linker (CBX-SS), oxi-dized alginate, N,N'-Bis(acryloyl)cystamine (BAC), methylene bis-acrylamide, and mixtures thereof.

In a particularly preferred embodiment, the impregnating fluid comprises curable monomers selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxymethyl)methyl acrylamide, bis-acrylamide, poly ethylene glycol diacrylate, N,N'-bis(acryloyl) cystamine, and mixtures thereof.

In a further particularly preferred embodiment, the impregnating fluid comprises water, and AAm and AA and MA and mBAA monomers. This embodiment is shown in FIG. 5.

In a further particularly preferred embodiment, the impregnating fluid comprises N-acryloyl glycinamide monomers. This embodiment is shown in FIG. 4 (*d*).

In a preferred embodiment, the curable monomers are curable by application of heat and/or irradiation and/or oxidizing agents and/or other common radical generators.

Curing Initiator:

Curing initiators are known per se. The main function of curing initiators is to initiate polymerisation of curable monomers. Preferably, a curing initiator is included in the impregnating fluid to initiate polymerisation of curable monomers within said impregnating fluid to thereby generate a mutually interpenetrating network. Further, curing initiators are preferably used to initiate polymerisation of monomers to thereby obtain the synthetic polymer comprised within the hydrogel support layer and/or the backing layer and/or an additional layer.

A broad range of curing initiators is known that function by a broad range of mechanisms, e.g. photoinitiators, oxidizing curing initiators, other common radical generators and enzymes such as horseradish peroxidase. Curing can also be initiated by application of heat-activatable curing initiators.

Photoinitiator: A photoinitiator is a molecule that creates reactive species (e.g. free radicals, cations or anions) when exposed to radiation (e.g. UV or visible light) and thus initiates polymerisation of curable monomers.

Suitable photoinitiators may be selected from the group consisting of Irgacure 2959 (2-hydroxy-4'-(2-hydroxyethoxy)-2-methylpropiophenone), lithium phenyl-2,4,6-trimethylbenzo-ylphosphinate, VA-086 2,2'-Azobis[2-methyl-N-(2-hydroxy-ethyl)propionamide, carboxy camphorquinone in combination with a suitable amine, camphorquinone in combination with a suitable amine, EosinY in combination with a suitable amine, roviflavin in combination with a suitable amine, fluorescein in combination with a suitable amine, alpha-ketoglutaric acid, 2-oxo-ketoglutaric acid.

Suitable amines may be selected from the group consisting of triethanolamine, ethylamine, N-vinylpyrrolidone, triethylamine, L-arginine, ethyl-4-N,N-dimethylaminobenzoate.

Oxidizing curing initiators: An oxidizing curing initiator is a molecule that creates reactive species (e.g. free radicals, cations or anions) through oxidative reactions and thus initiates polymerisation of curable monomers. Suitable oxidizing curing initiators may be selected from the group consisting of $NaIO_4$ and horseradish peroxidase.

Suitable other common radical generators may be selected from the group consisting of azaisobutyronitril, ammonium persulfate and other persulfate salts such as sodium persulfate and potassium persulfate.

In a preferred embodiment, curing initiators are included in the impregnating fluid and/or used to generate a synthetic polymer comprised within the hydrogel support layer and/or the backing layer and/or an additional layer, and curing initiators are selected from the group consisting of Irgacure 2959, Eosin Y in combination with triethanolamine or N-vinylpyrrolidone and lithium phenyl-2,4,6-trimethylbenzoyl phosphinate.

The skilled person would know and/or select a suitable curing initiator that is adapted for curing the monomers that are included in the impregnating fluid to form a mutually interpenetrating network and/or to generate a polymer comprised within the hydrogel support layer and/or the backing layer and/or an additional layer.

Functional Components/Sensing Components:

In certain preferred embodiments, the patch further comprises functional components which are detectable, preferably by a noninvasive test method. Accordingly, these functional components provide a function of a sensing component. Thus, said sensing components enable monitoring of the application site, specifically a sutured or stapled site, and thereby alleviate the need for artificial drains to the patient's body. Further, said sensing components mitigate the risk for septic peritonitis or other adverse events in the case of leakage of a sutured or stapled soft tissue reconnection site due to early detection of said leakage. A broad range of sensing components can be used in the context of the present invention.

The terms "monitoring" and "monitor" as used in the context of the present invention relates to the detection of leak formation at a suture site or stapled site, in particular in the abdominal region, more particularly an anastomosis site. Such detection of leak formation means that so-called "sensing components" are transformed/activated or released from the patch upon contact with biological fluids, leading to a detectable signal. Hence, typically a detectable signal relates to a change in signal upon contact with a biological fluid.

"Transformation/activation" of a sensing component for example refers to the collapse of a gas containing structure (e.g. embedded gas-containing vesicles) or the generation of a detectable component, such as the generation of $Fe^{3+}$ as a dissolution product of $Fe_2O_3$ or the generation of $CO_2$ from carbonates (e.g. sodium bicarbonate) upon contact with a biological fluid.

A detectable signal may be generated by compounds that are embedded in the hydrogel support layer and/or the backing layer and/or an additional encasing sensing matrix and that are activated/transformed and/or released from the patch upon contact with a biological fluid. In specific embodiments, said release of sensing components occurs due to swelling of the polymer matrix or cleavage of the sensing component from its polymer matrix (full or partial degradation of said polymer matrix) located within the hydrogel support layer and/or the backing layer and/or the encasing sensing matrix.

Detection can be achieved for example upon application of ultrasound, computer tomography (CT), magnetic resonance imaging (MRI) or radio-frequency identification (RFID).

In some embodiments, detectable gas bubbles are generated by compounds that are embedded in the hydrogel support layer and/or the backing layer and/or an additional encasing sensing matrix and that lead to gas formation upon contact with a biological fluid, e.g. $CaCO_3$ powder or $NaHCO_3$ powder.

A detectable ultrasound signal may also be generated by hydrophobic aerogels, particularly selected from alginate—sodium cholate aerogels and superhydrophobic silica aerogel particles. Superhydrophobic silica aerogel particles are commercially available (Lumira).

Suitable compounds that lead to a detectable signal upon application of ultrasound may be selected from the group consisting of gas-containing vesicles and/or gas-containing microbubbles of natural or synthetic origin, carbonates such as $CaCO_3$, $NaHCO_3$, $Na_2CO_3$, and other inorganic nanoparticles such as metal or metal oxide, in particular ZnOx nanoparticles (x between 0 to 2, e.g. 1), carbides, and hydrophobic aerogels, such as alginate—sodium cholate aerogels and superhydrophobic silica aerogel particles.

In some embodiments, carbonates are carbonate nanoparticles. However, carbonates are not limited to carbonate nanoparticles but can vary in size.

Such detectable ultrasound signal can be generated by various means, e.g. the generation or release of gas bubbles (e.g. $CO_2$ generated from carbonates upon contact with intestinal fluid) or the collapse or a structural alteration of the membrane (e.g. degradation of crosslinks in the membrane) of gas containing structures, such as gas-containing vesicles or synthetic gas-containing microbubbles, leading to a detectable change in ultrasound contrast. The change in ultrasound contrast is detectable e.g. by harmonic imaging and subharmonic imaging.

The release or generation of gas containing structures is also referred to herein as a "turn-on" type ultrasound signal because the generation or release of said gas containing structure leads to the generation of an ab initio not detectable signal. For example, in case of $NaHCO_3$ particles, $CO_2$ is released upon contact with gastric fluid. In a preferred embodiment, $NaHCO_3$ is used as a sensing component. This embodiment is described in example 3b and shown in FIG. 4 (*c*).

Alternatively, the collapse of gas containing structures is also referred to herein as a "turn-off" type ultrasound signal because said collapse leads to the loss of an ab initio detectable signal. For example, gas-containing vesicles and/or synthetic gas-containing microbubbles that are embedded in the patch (and are ab initio detectable by ultrasound imaging) are collapsed as a result of the contact with biological fluid.

As used herein, the term "gas-containing vesicles" refers to gas-filled protein nanostructures that are isolated from natural cyanobacterial, particularly *Anabaena flos-aquae* (Ana) and haloarchaeal, particularly *Halobacterium salinarum*, host organisms (Halo) or from genetically engineered organisms, such as *E. coli* expressing a heterologous gas vesicle gene cluster. Such gas-containing vesicles typically have a diameter of approximately 100-900 nanometers. The hollow gas interior is enclosed by a protein shell of typically 1-5 nm shell that is permeable to gas but excludes liquid water. Owing to their physical properties, gas-containing vesicles are known to serve as highly sensitive imaging agents for ultrasound and magnetic resonance imaging (MRI).

As used herein, the term "gas-containing microbubbles" refers to synthetic microstructures having a surrounding membrane of phospholipids or polymers, which encapsulates a gas, such as air, oxygen or hexafluorosulfide and a bubble size of 0.1-50 micrometer.

It is to be understood that the terms "turn-on"/"turn-off" do not imply a binary situation but rather indicate a detectable change of a signal.

In a preferred embodiment, gas-containing vesicles and/or synthetic gas-containing microbubbles are used as a sensing component. This embodiment is described in example 3a and shown in FIG. 3 (*b*) and FIG. 4 (*b*).

In a particularly preferred embodiment, gas-containing vesicles are used as a sensing component.

In a further preferred embodiment, inorganic nanoparticles, in particular ZnOx (x between 0 to 2, e.g. 1), $Fe_2O_3$ and/or $Fe_3O_4$ nanoparticles, are used as a sensing component.

Suitable compounds that lead to a detectable signal upon application of CT may be selected from the group consisting of metal or metal oxide nanoparticles such as iron or iron oxide, zinc oxide, zinc ferrite, tantalum or tantalum oxide, bismuth oxide or ferrite, Au nanoparticles, CaCO3, BaCO3 and PVP-iodine.

Suitable compounds that lead to a detectable signal upon application of CT (and/or MRI) may be selected from the group consisting of metal or metal oxide nanoparticles, such as iron or iron oxide, zinc oxide, zinc ferrite, manganese oxide, terbium oxide, gadolinium oxide, surface-modified metal and/or metal oxide nanoparticles, and Gd complexes.

In a preferred embodiment, tantalum oxide nanoparticles are used as a sensing component (cf. example 3e and FIG. 12).

Suitable compounds that lead to a detectable signal upon application of RFID may be selected from the group consisting of TWC-401-100 Mifare S50, cellulose acetate, copper wire, sodium carboxymethylcellulose, polyimide or magnesium wire.

However, in light of the above disclosure, it is clear to the skilled person that various other sensing components can be used in the context of the present invention.

The skilled person, taking into consideration the common technical knowledge in the medical field, would know and/or select the additional sensing component in light of the disease/condition to be treated.

In a preferred embodiment, said sensing components are present in the hydrogel support layer.

In another preferred embodiment, said sensing components are present in the backing layer.

In another preferred embodiment, said sensing components are present in the hydrogel support layer and the backing layer.

In another preferred embodiment, said sensing components are present in an additional layer (FIG. 2, b: 1.3). Said additional layer comprising sensing components is also referred to as an encasing sensing matrix.

In a preferred embodiment, the sensing components are finely dispersed within said layer or matrix.

Again, said encasing sensing matrix is present in the patch in addition to the hydrogel support layer. The encasing sensing matrix may comprise synthetic and/or natural polymers that can be degradable or non-degradable. In some of these embodiments, the encasing sensing matrix comprises a synthetic hydrogel that can be degradable or non-degradable. In general, all components that are suitable in the context of the hydrogel support layer are also suitable for the encasing sensing matrix. For example, synthetic hydrogels comprising the same monomeric units, including crosslinkers, as described for the hydrogel support layer are also suitable for synthetic hydrogels in the context of the encasing sensing matrix.

For example, an encasing sensing matrix consisting of a hydrogel comprising 20 wt % AAm and 20% vol gas-containing vesicles crosslinked with BAC is degradable by pancreatin, which is a major enzyme of the intestinal fluid.

A suitable encasing sensing matrix may be selected from the group consisting of synthetic polymers comprising one or more monomeric units selected from the group consisting of methacrylates, acrylates, vinyls, thiols, polyurethane forming monomers and mixtures thereof. Preferably, the monomeric units are selected from the group consisting of methacrylates, acrylates, vinyls, thiols and mixtures thereof.

In some embodiments, the encasing sensing matrix comprises one or more synthetic polymers and does not comprise a natural polymer.

In some embodiments, the encasing sensing matrix comprises one or more natural polymers and does not comprise a synthetic polymer.

In some embodiments, the encasing sensing matrix comprises one or more natural polymers and one or more synthetic polymers.

Suitable natural polymers may be selected from the group consisting of alginate, chitosan, agar, carboxymethylcellulose, gelatine, bovine serum albumin, human serum albumin.

In some embodiments, the encasing sensing matrix additionally comprises natural and/or synthetic additives.

Suitable natural additives may be selected from the group consisting of dextran, heparin, hyaluronic acid, gellan gum, kappacarraggennans, butyric acid, caproic acid, caprylic acid, capric acid, lauric acid, myristic acid, palmitic acid, palmitoleic acid, stearic acid, oleic acid, ricinoleic acid, vaccenic acid, linoleic acid, alpha-linolenic acid, arachidic acid, gadoleic acid and gamma-linolenic acid.

Suitable synthetic additives may be selected from the group consisting of polyacrylic acid, PHPMA, PVA, PCL, PHEMA, PVDF, polyethylene glycol (PEG 400, 600, 1000), polydopamine and polygallic acid.

In some embodiments, the encasing sensing matrix comprises acrylated polymers such as acrylated elastin, acrylated HEMA, acrylated albumin, acrylated alginate, acrylated HSA, and mixtures thereof.

Preferably, said additives within the encasing sensing matrix are natural additives selected from the group consisting of capric acid, lauric acid, myristic acid, palmitic acid, palmitoleic acid, stearic acid, oleic acid, ricinoleic acid, vac-cenic acid, linoleic acid, alpha-linolenic acid, arachidic acid, gadoleic acid and gamma-linolenic acid.

More preferably, said additives within the encasing sensing matrix are natural additives selected from the group consisting of stearic acid, myristic acid and palmitic acid.

In a preferred embodiment, the encasing sensing matrix comprises a synthetic polymer comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl)methyl acrylamide, bis-acrylamide, poly ethylene glycol diacrylate, N,N'-bis(acryloyl) cystamine, and mixtures thereof.

In a preferred embodiment, the encasing sensing matrix comprises one or more natural polymers selected from the group consisting of carboxymethylcellulose, alginate, agar, bovine serum albumin, human serum albumin and gelatine.

In one embodiment, the patch comprises AAm and AA and MA and mBAA (crosslinker) monomeric units (p(AAm-AA-MA) hydrogel). This embodiment is described in example 1 and shown in FIG. 3 (*a*), FIG. 5 and FIG. 6.

In one embodiment, the patch comprises AAm and gas-containing vesicles (sensing component). This embodiment is described in example 3a and shown in FIG. 3 (*b*) and FIG. 4 (*b*).

In one embodiment, the patch comprises bovine serum albumin, and glutaraldehyde (crosslinker), and gas-containing vesicles (sensing component). This embodiment is shown in FIG. 3 (*c*).

In one embodiment, the patch comprises agar, and $NaHCO_3$ (sensing component). This embodiment is described in example 3b and shown in FIG. 4 (*c*).

In one embodiment, the patch consists of a hydrogel support layer comprising monomeric units of N-acryloyl glycinamide, and an encasing sensing matrix comprising AAm monomeric units, and gas-containing vesicles (sensing component). In this embodiment, the impregnating fluid comprises N-acryloyl glycinamide curable monomers. This embodiment is shown in FIG. 4 (*d*).

In one embodiment, the patch comprises AAm, and mBAA (cross-linker) monomeric units, and ZnO nanoparticles (sensing and therapeutic component). This embodiment is described in example 4 and shown in FIG. 7.

In specific embodiments, said activation/transformation or release of sensing components occurs due to swelling, degrada-tion and/or a structural change, i.e. dissolving and/or partial dissolution, of the encasing sensing matrix and/or said sensing component located within the hydrogel support layer and/or the backing layer and/or the encasing sensing matrix. For example, gastric fluid may lead to degradation of the encasing sensing matrix whereas bile fluid may lead to the solubilisation of components of the encasing sensing matrix.

Functional Components/Therapeutic Components:

In certain preferred embodiments of the invention, the patch additionally comprises one or more therapeutically active components.

In a preferred embodiment, said functional components are therapeutic components that are suitable for treating a leak at an anastomosis site, e.g. therapeutic components with antibiotic or wound healing activity.

In preferred embodiments, said therapeutic components that are suitable for treating a leak at an anastomosis site, e.g. antimicrobials, are released from the patch upon contact with intestinal fluid, e.g. through swelling and/or (full or partial) degradation of the hydrogel matrix.

Suitable therapeutic components with antimicrobial activity may be selected from the group consisting of antimicrobials including beta-lactams (penicillins), carbapenems (beta-lactamase-resistant beta-lactams), cephalosporins (semi-synthetic beta-lac-tams), and quinolones (e.g. ciprofloxacin), glycopeptides (e.g. vancomycin), aminoglycosides (e.g. gentamycin), and mupirocin and mixtures thereof in free or immobilized form, including biopolymer grafted antimicrobials, such as alginate grafted gentamycin. Further therapeutic components include metal and/or metal oxide nanoparticles or salts, particularly Ag/AgOx, ZnOx, Cu/CuOx, GaOx, cerium chloride, supported metal and metal oxide nanoparticles, including SiO2/Ag, SiO2/Cu, SiO2/ZnOx, functionalized metal and/or metal oxide nanoparticles, and mixtures thereof, wherein x can be between 0 to 2, e.g. 1.

Preferably, said therapeutic components are selected from the group consisting of Ag, ZnOx (x between 0 to 2, e.g. 1).

For example, such therapeutic components are suitable for the treatment of septic peritonitis that may result from leaking of bacteria-containing intestinal fluid.

In a further preferred embodiment, said therapeutic components are suitable to support wound healing at a sutured or stapled site, particularly an anastomosis site.

Therapeutic components that are suitable to support wound healing at a sutured or stapled site, particularly an anastomosis site may be selected from the group consisting of growth factors such as platelet-derived growth factor (PDGF), transforming growth factor-β1 (TGF-β1), vascular endothelial growth factor (VEGF), fibroblast growth factor (FGF), growth hormone (GH), flavonoids, metal oxide nanoparticles and salts, alginate, and peptides such as RGD, Tβ 4, AP-57, and mixtures thereof. The above compounds are integrated into the hydrogel either by passive loading, cross-linking, conjugation to a natural or synthetic polymer backbone or by incorporating drug loaded liposomes or polymersomes.

However, in light of the above disclosure, it is clear to the skilled person that various other therapeutic components can be used in the context of the present invention.

The skilled person, taking into consideration the common technical knowledge in the medical field, would know and/or select the additional therapeutic component in light of the disease/condition to be treated.

In a preferred embodiment, said therapeutic components are present in the hydrogel support layer.

In another preferred embodiment, said therapeutic components are present in the backing layer.

In another preferred embodiment, said therapeutic components are present in the hydrogel support layer and the backing layer.

In another preferred embodiment, said therapeutic components are present in an additional layer (FIG. 2, b: 1.3). Said additional layer comprising therapeutic components is also referred to as an encasing therapeutic matrix.

In a preferred embodiment, the therapeutic components are finely dispersed within said layer or matrix.

Again, said encasing therapeutic matrix is present in the patch in addition to the hydrogel support layer. Suitable encasing therapeutic matrices are generally the same as described above for encasing sensing matrices.

In a preferred embodiment, the encasing therapeutic matrix comprises a synthetic polymer comprising monomeric units selected from the group consisting of 2-acryloyloxy)ethyl)trimethylammonium chloride), acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxymethyl)methyl acrylamide, bis-acrylamide, poly ethylene glycol diacrylate, N,N'-bis(acryloyl) cystamine, and mixtures thereof.

In a preferred embodiment, the encasing therapeutic matrix comprises one or more natural polymers selected from the group consisting of carboxymethylcellulose, alginate, agar, bovine serum albumin, human serum albumin, gelatine.

In specific embodiments, said release of therapeutic components occurs due to swelling of the polymer matrix or cleavage of the therapeutic component from its polymer matrix (full or partial degradation of said polymer matrix) located within the hydrogel support layer and/or the backing layer and/or the encasing therapeutic matrix.

Thus, the present invention provides suture and/or staple supports and/or sealing materials that are capable of releasing therapeutic components, such as antibiotics, upon contact with biological fluids, in particular leaking of intestinal, gastric, biliary fluids or cerebrospinal fluid or other biological fluids, hence mitigating the risk for sepsis or other adverse events.

Additives impregnating fluid: In certain embodiments, the impregnating fluids further comprises transglutaminase. Transglutaminase may further increase adhesion to tissues by mediating covalent bond formation between the tissue and components of the patch and/or the impregnating fluid. Transglutaminase is typically used as a meat-glue.

However, in other embodiments, addition of transglutaminase is not required.

In certain embodiments, the impregnating fluid comprises natural and/or synthetic additives. Such additives may be added to adjust the viscosity of the impregnating fluid and/or improve adhesion to tissue (e.g. kappacarraggennans) and/or support wound healing (e.g. alginate, hyaluronic acid, chitosan). Suitable natural additives may be selected from the group consisting of alginate, chitosan, carboxymethylcellulose, dextran, heparin, hyaluronic acid, gellan gum, kappacarraggennans, dopamine, caffeic acid, gallic acid, tryptophan, catechin, ellargic acid, nitrodopamine, NitroDOPA, mimosine, gallic acid grafted chitosan, caffeic acid grafted chitosan, dopamine grafted alginate, and mixtures thereof.

Preferably, natural additives are selected from the group consisting of alginate, chitosan, carboxymethylcellulose, dextran, heparin, kappacarraggennans, caffeic acid, gallic acid, gallic acid grafted chitosan, caffeic acid grafted chitosan, dopamine grafted alginate, and mixtures thereof.

Suitable synthetic additives may be selected from the group consisting of polyacrylic acid, PHPMA, PVA, PCL, PHEMA, PVDF, polyethylene glycol (PEG 400, 600, 1000), polydopamine, polygallic acid, and mixtures thereof.

Preferably, synthetic additives are selected from the group consisting of polyacrylic acid, PHPMA, PVA, PHEMA, polyethylene glycol (PEG 400, 600, 1000), polydopamine, polygallic acid, and mixtures thereof.

Additives impregnating fluid/ionic strength adjusting media incl. buffers and salts: In certain embodiments, the impregnating fluid additionally comprises ionic strength adjusting media, including buffers and salts. Suitable ionic strength adjusting media may be selected from the group consisting of PBS, isotonic NaCl solution, sugar solution, polyvidone iodine solution, citrate buffer, isocitrate buffer, EDTA (including EDTA salts), borate salts, Epsom salts, sodium periodate and mixtures thereof.

Additives/Surfactants: In certain embodiments, the impregnating fluid additionally comprises surface active substances, including non-ionic, cationic, anionic and amphoteric surfactants. Suitable surface active substances may be selected from the group consisting of choline-geranate, DABCO-Br, morpholinium-Br, methylpyrrolidinium sulfate, polyoxyethylene sorbitan monooleate, sorbitan laurate, sodium dodecyl sulfate, and mixtures thereof.

In view of the above disclosure, the following combination of materials was found particularly beneficial for the inventive kit of parts:

In a 1$^{st}$ embodiment, the patch consists of a hydrogel support layer, and the inventive kit of parts comprises (i) a hydrogel support layer comprising a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine; and (ii) an impregnating fluid comprising curable monomers selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine. The impregnating fluid further comprises curing initiators, preferably selected from the group consisting of Irgacure 2959, Eosin Y in combination with tri-ethanolamine and lithium phenyl-2,4,6-trimethylbenzoyl phosphinate.

In a 2$^{nd}$ embodiment, the patch consists of a hydrogel support layer and a backing layer, and the inventive kit of parts comprises (i) a hydrogel support layer comprising a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine; and (ii) an impregnating fluid comprising curable monomers selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine. The impregnating fluid further comprises curing initiators, preferably selected from the group consisting of Irgacure 2959, Eosin Y in combination with tri-ethanolamine and lithium phenyl-2,4,6-trimethylbenzoyl phosphinate.

(iii) The backing layer comprises a non-adhesive polymer comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris(hydroxymethyl)methyl acrylamide, bis-acrylamide, poly ethylene glycol diacrylate, N,N'-bis(acryloyl) cystamine; and/or one or more natural polymers selected from the group consisting of carboxymethylcellulose and alginate.

In a 3$^{rd}$ embodiment, the patch consists of a hydrogel support layer and a backing layer and further contains sensing components. The inventive kit of parts comprises (i) a hydrogel support layer comprising a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine; and (ii) an impregnating fluid comprising curable monomers selected form the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl)methyl acrylamide, bis-acrylamide, poly ethylene glycol diacrylate, N,N'-bis(acryloyl) cystamine. The impregnating fluid further comprises curing initiators, preferably selected from the group consisting of Irgacure 2959, Eosin Y in combination with tri-ethanolamine and lithium phenyl-2,4,6-trimethylbenzoyl phosphinate.

(iii) The backing layer comprises a non-adhesive polymer comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris(hydroxymethyl)methyl acrylamide, bis-acrylamide, poly ethylene glycol diacrylate, N,N'-bis(acryloyl) cystamine and/or one or more natural polymers selected from the group consisting of carboxymethylcellulose and alginate.

(iv) The sensing components are preferably selected from the group consisting of $NaHCO_3$, $Na_2CO_3$, $CaCO_3$, gas-containing vesicles and/or synthetic gas-containing microbubbles, preferably gas-containing vesicles, iron oxide nanoparticles and zinc oxide nanoparticles.

In this embodiment, the patch does not comprise a therapeutic component.

In a 4$^{th}$ embodiment, the patch consists of a hydrogel support layer and a backing layer and further contains sensing components and therapeutic components. The inventive kit of parts comprises (i) a hydrogel support layer comprising a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl)methyl acrylamide, bis-acrylamide, poly ethylene glycol diacrylate, N,N'-bis(acryloyl) cystamine; and (ii) an impregnating fluid comprising curable monomers selected form the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl)methyl acrylamide, bis-acrylamide, poly ethylene glycol diacrylate, N,N'-bis(acryloyl) cystamine. The impregnating fluid further comprises curing initiators, preferably selected from the group consisting of Irgacure 2959, Eosin Y in combination with tri-ethanolamine and lithium phenyl-2,4,6-trimethylbenzoyl phosphinate.

(iii) The backing layer comprises a non-adhesive polymer comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxymethyl)methyl acrylamide, bis-acrylamide, poly ethylene glycol diacrylate, N,N'-bis(acryloyl) cystamine and/or one or more natural polymers selected from the group consisting of carboxymethylcellulose and alginate.

(iv) The sensing components are preferably selected from the group consisting of $NaHCO_3$, $Na_2CO_3$, $CaCO_3$, gas-containing vesicles, iron oxide nanoparticles, zinc oxide nanoparticles.

(v) The therapeutic components are selected from the group consisting of antimicrobials and compounds that support wound healing.

Thus, in this embodiment, the patch comprises sensing components and therapeutic components.

In a 5$^{th}$ embodiment, the patch consists of a hydrogel support layer and a backing layer and further contains therapeutic components. The inventive kit of parts comprises (i) a hydrogel support layer comprising a non-degradable, synthetic hydrogel comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl)methyl acrylamide, bis-acrylamide, poly ethylene glycol diacrylate, N,N'-bis(acryloyl) cystamine; and (ii) an impregnating fluid comprising curable monomers selected form the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl)methyl acrylamide, bis-acrylamide, poly ethylene glycol diacrylate, N,N'-bis(acryloyl) cystamine. The impregnating fluid further comprises curing initiators, preferably selected from the group consisting of Irgacure 2959, Eosin Y in combination with tri-ethanolamine and lithium phenyl-2,4,6-trimethylbenzoyl phosphinate.

(iii) The backing layer comprises a non-adhesive polymer comprising monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxymethyl)methyl acrylamide, bis-acrylamide, poly ethylene glycol diacrylate, N,N'-bis(acryloyl) cystamine and/or one or more natural polymers selected from the group consisting of carboxymethylcellulose and alginate.

(v) The therapeutic components are selected from antimicrobials and compounds that support wound healing.

In this embodiment, the patch comprises therapeutic components but does not comprise sensing components.

In the 3$^{rd}$ and 4$^{th}$ embodiment described above, the patch optionally comprises an additional encasing sensing matrix comprising a synthetic polymer comprising monomeric units preferably selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxyme-thyl)methyl acrylamide, bis-acrylamide, poly ethylene glycol di-acrylate, N,N'-bis(acryloyl) cystamine and mixtures thereof; and/or one or more natural polymers preferably selected from the group consisting of carboxymethylcellulose, alginate, agar, bovine serum albumin, human serum albumin, gelatine, and mixtures thereof. Said encasing sensing matrix further optionally includes additives, preferably selected from the group consisting of stearic acid, myristic acid and palmitic acid.

In the 4$^{th}$ and 5$^{th}$ embodiment described above, the patch optionally comprises an additional encasing therapeutic matrix comprising a synthetic polymer comprising monomeric units preferably selected from the group consisting of 2-acryloyloxy) ethyl) trimethylammonium chloride), acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris(hydroxyme-thyl)methyl acrylamide, bis-acrylamide, poly ethylene glycol di-acrylate, N,N'-bis(acryloyl) cystamine, and mixtures thereof; and/or one or more natural polymers selected from the group consisting of carboxymethylcellulose, alginate, agar, bovine serum albumin, human serum albumin, gelatine and mixtures thereof. Said encasing therapeutic matrix further optionally includes additives, preferably selected from the group consisting of stearic acid, myristic acid and palmitic acid.

In a particularly preferred embodiment, the patch comprises a hydrogel support layer comprising a non-degradable, synthetic poly(2-acrylamido-2-methyl-1-propanesulfonic acid) (PAMPS) hydrogel and a backing layer comprising a non-adhesive poly(N-hydroxyethylacrylamide) (PNHEA) polymer. The impregnating fluid comprises water as pharmaceutically acceptable fluid and N-acryloyl glycinamide curable monomers.

Alternatively, instead of PNHEA, the backing layer may comprise a hydrophilic polyurethane, preferably an ether-based hydrophilic polyurethane, such as commercially available Hydromed D4, as the non-adhesive polymer.

Patch:

The patch comprised within the inventive kit of parts comprises a hydrogel support layer and may further comprise additional layers and/or functional components as described above.

In view of the above disclosure, the following patch setups (FIG. 2) comprising one or more groups of functional components were found particularly beneficial for the inventive kit of parts:

In a first embodiment, the patch consists of a hydrogel support layer and a backing layer. Said hydrogel support layer comprises one or more groups of functional components ((6) and (7) in FIG. 2*a*). In this embodiment, the backing layer does not comprise functional components (FIG. 2*a*).

In a second embodiment, the patch consists of a hydrogel support layer and a backing layer. Said hydrogel support layer comprises one group of functional components, and said backing layer comprises another group of functional components. Accordingly, both said hydrogel support layer and said backing layer comprise different functional components (FIG. 2*b*, left).

In a third embodiment, the patch consists of a hydrogel support layer and a backing layer and an additional layer. In this embodiment said additional layer ("encasing matrix") comprises one or more groups of functional components. In this embodiment, the hydrogel support layer and the backing layer do not comprise functional components (FIG. 2*b*, middle).

In a fourth embodiment, the patch consists of a hydrogel support layer and a backing layer. In this embodiment, the hydrogel support layer comprises one or more groups of functional components and the backing layer comprises one or more groups of functional components. Accordingly, in this embodiment both, the functional components are present in both, the hydrogel support layer and the backing layer (FIG. 2*b*, right).

The kit of parts described generally and in any variants herein is suitable for a broad range of applications. However, different applications and/or specific application sites may require different shapes and/or sizes of the patch that is included in said kit of parts.

Thus, in embodiments of the invention, the patch has the shape of a disk.

In further embodiments, the patch has a cylindrical shape.

In further embodiments, the patch has a rectangular shape.

In further embodiments, the patch has a rhombohedral shape.

In further embodiments, the patch has a trapezoidal shape.

In further embodiments, the patch has the shape of a ring.

In further embodiments, the patch has a triangular shape.

In further embodiments, the patch has a thickness of 0.5-40 mm.

In further embodiments, the patch has a length of 5-400 mm.

In further embodiments, the patch has a width of 5-70 mm.

The skilled person, taking into consideration the common technical knowledge in the medical field, would know and/or select the appropriate shape and size of the patch in light of the disease/condition to be treated.

For example, a patch with a cylindrical shape, a thickness of 2-10 mm, a length of 30-100 mm a diameter of 20-50 mm is suitable for e.g. support of sutured or stapled regions of the small or large intestine.

For example, a patch with a rectangular shape, a thickness of 1-30 mm, a length of 40-200 mm and a width of 10-30 mm is suitable for e.g. support of sutured or stapled regions of the small or large intestine or oesophageal resection closing sutures or staples.

For example, a patch with a ring shape, a thickness of 1-10 mm, an inner diameter of 10-50 mm and an outer diameter of 50-100 with is suitable for e.g. portacaval anastomosis.

For example, a patch with a triangular shape, a thickness of 1-15 mm, and a side length of 50-100 mm is suitable for e.g. biliary diversion reconnections.

In other embodiments, the patch is provided with a rectangular shape that can be cut by the surgeon to the appropriate shape and size, for example with a length of about 1-15 cm, such as about 3, 4.8, 5, 9.5 or 10 cm, and with a width of about 1-10 cm, such as about 2, 2.5, 4.8 or 5 cm.

In a second aspect, the invention relates to a process for manufacturing a kit as defined in claim 1. Manufacturing of hydrogels in the form of a sheet-like material is a technology known per se. Also, the preparation of impregnating fluids is a known technology. However, applying these technologies to the kit of parts with the purpose of sealing and immobilizing said hydrogel patch to tissue as described herein is unknown until now. It is considered beneficial that known manufacturing technologies are applicable to the inventive kit of parts. Adapting known equipment and selecting appropriate starting materials is within the ordinary skill.

In a preferred embodiment, the patch is manufactured by (a) providing a solution comprising monomers that are part of the hydrogel support layer and a curing initiator adapted for curing the monomers (as described above), and (b) subjecting the solution to 3D-printing or mold-curing step to thereby obtain a sheet-like material. If required, the thus obtained sheet like material is in step (c) cut to obtain a patch with an appropriate shape and appropriate dimensions. In step (d), the patch is packaged for transport and/or sale. Optionally, the sheet-like material obtained in (b) is purified by dialysis or another method, e.g. low intensity UV light exposure or heat to remove residual monomers.

In a preferred embodiment, in step (a), an additional solution comprising monomers that are part of the backing layer and a curing initiator adapted for curing the monomers (as described above) is provided.

In a preferred embodiment, in step (a), an additional solution comprising monomers or polymers that are part of an additional hydrogel layer, i.e. an encasing sensing matrix or an encasing therapeutic matrix, a curing initiator adapted for curing the monomers (as described above), as well as sensing components and/or therapeutic components, is provided.

In a preferred embodiment, the impregnating fluid is manufactured by combining the components such as a pharmaceutically acceptable liquid (water and/or glycerol), curable monomers, a curing initiator adapted for curing the monomers (as described above) and/or additives, to obtain a fluid.

In a preferred embodiment, the impregnating fluid is packaged for transport and/or sale.

In a third aspect, the invention relates to the use of a kit of parts and the use of an impregnating fluid described generally and in any variants herein. In particular, the invention relates to the use of said kit of parts and the use of the impregnating fluid in surgery.

In a particular embodiment, the invention relates to the use of said kit of parts as suture and/or staple supports, e.g. in the abdominal region, such as for the treatment of intestinal anastomosis, stomach resection, gallbladder anastomosis, gallbladder resection, liver resection, colon resection, colon anastomosis, pancreas resection, pancreas anastomosis, portacaval anastomosis (connection to liver adjacent organs), or oesophageal anastomosis.

In a further particular embodiment, the invention relates to the use of said kit of parts for sealing an artificial stoma, e.g. a temporary stoma or a permanent stoma in a subject-in-need thereof.

In a preferred embodiment, the use of said kit of parts comprises the following steps in the order as indicated:

a) Contacting the patch with the impregnating fluid for a period of time defined by the dimensions of the patch.

b) Applying the impregnating fluid to the sutured site, stapled site or stoma site: Immediately after termination of the incubation period (i.e. impregnation of the patch with the impregnating fluid) and just before application of the patch to the sutured site or stapled site or stoma site, the tissue is contacted with the impregnating fluid. Typically, the tissue is contacted only with a small quantity of the impregnating fluid. It is considered an advantage that only minor amounts of impregnating fluid ensure reliable adhesion of the patch on the soft tissue to be treated. Suitable are, for example, less than 5 ml fluid for 1 $cm^2$ tissue to be treated; even 0.15 ml fluid for 1 $cm^2$ tissue to be treated may be sufficient.

c) Applying the patch to the sutured site, stapled site or stoma site: The impregnated patch is then placed on the sutured or stapled site or stoma site. Advantageously, the patch is held in place, e.g. by using a light transparent plate, for a predefined amount of time to thereby optimize patch-tissue contact. Suitable are for example 5 sec-5 min. This ensures the patch adapts to the surface of the soft tissue and the fluid interpenetrates both, patch and tissue.

d) The curable monomers within the impregnating fluid are then briefly irradiated or otherwise cured in place. The resulting polymer network spans the patch and suture/stapled site or stoma site and thus fixates the patch on the suture/stapled site or stoma site.

Further, the invention relates to the use of a kit of parts as defined in any of claims 1 to 11 for the manufacturing of a therapeutic product for the treatment of sutured sites, stapled sites or artificial stoma sites. The therapeutic product mitigates the risk of adverse effects of suture, staple or artificial stoma breakage or leakage.

In particular, the treatment of sutured or stapled sites includes the treatment of intestinal anastomosis; stomach resection; oesophageal anastomosis, bile duct anastomosis, gallbladder anastomosis; gallbladder resection; liver resection; colon resection; colon anastomosis; pancreas resection; pancreas anastomosis; or portacaval anastomosis and the treatment of stoma comprises temporary stoma or permanent stoma.

Further, the invention relates to the use of an impregnating fluid in a surgical method for adhering a patch to a sutured site, a stapled site or a stoma site of a subject in need thereof, wherein the impregnating fluid comprises a pharmaceutically acceptable liquid selected from water and/or glycerol, and curable monomers. The patch comprises a hydrogel support layer comprising a non-degradable, synthetic hydrogel as described above. Preferably, the surgical method is sealing of an artificial stoma, such as sealing of a temporary stoma or a permanent stoma.

Further, the invention relates to the use of the therapeutic product described above, wherein the therapeutic product comprises instructions for performing the following steps in the order as indicated:

a) Contacting the patch with the impregnating fluid for a period of time defined by the dimensions of the patch.

b) Applying the impregnating fluid to the sutured site, stapled site or stoma site: Immediately after termination of the incubation period (i.e. impregnation of the patch with the impregnating fluid) and just before application of the patch to the sutured site or stapled site or stoma site, the tissue is contacted with the impregnating fluid. Typically, the tissue is contacted only with a small quantity of the impregnating fluid. As described above, it is considered an advantage that only minor amounts of impregnating fluid ensure reliable adhesion of the patch on the soft tissue to be treated. Suitable are, for example, less than 5 ml fluid for 1 $cm^2$ tissue to be treated; even 0.15 ml fluid for 1 $cm^2$ tissue to be treated may be sufficient.

c) Applying the patch to the sutured site, stapled site or stoma site: The impregnated patch is then placed on the sutured or stapled site or stoma site. As described above, advantageously, the patch is held in place for a predefined amount of time. Suitable are for example 5 sec-5 min. This ensures the patch adapts to the surface of the soft tissue and the fluid interpenetrates both, patch and tissue.

d) The curable monomers within the impregnating fluid are then briefly irradiated or otherwise cured in place. The resulting polymer network spans the patch and suture/stapled site or stoma site and thus fixates the patch on the suture/stapled site or stoma site.

Further, the invention relates to a method of treating a sutured site, stapled site or stoma site in a subject in need thereof, the method comprising the steps of applying a kit of parts as defined in any of claims 1 to 11 to a sutured or stapled site or stoma site.

In particular embodiments, the sutured or stapled site is selected from intestinal anastomosis; stomach resection; oesophageal anastomosis; bile duct anastomosis; gallbladder anastomosis; gallbladder resection; liver resection; colon resection; colon anastomosis; pancreas resection; pancreas anastomosis; or portacaval anastomosis. In further particular embodiments, the stoma site is selected from temporary stoma or permanent stoma.

The invention further relates to a method as described above wherein the method comprises the following steps in the order as indicated:

a) Contacting the patch with the impregnating fluid for a period of time defined by the dimensions of the patch.

b) Applying the impregnating fluid to the sutured site, stapled site or stoma site: Immediately after termination of the incubation period (i.e. impregnation of the patch with the impregnating fluid) and just before application of the patch to the sutured site or stapled site or stoma site, the tissue is contacted with the impregnating fluid. Typically, the tissue is contacted only with a small quantity of the impregnating fluid. As described above, it is considered an advantage that only minor amounts of impregnating fluid ensure reliable adhesion of the patch on the soft tissue to be treated. Suitable are, for example, less than 5 ml fluid for 1 $cm^2$ tissue to be treated; even 0.15 ml fluid for 1 $cm^2$ tissue to be treated may be sufficient.

c) Applying the patch to the sutured site, stapled site or stoma site: The impregnated patch is then placed on the sutured site or stapled site or stoma site. As described above, advantageously, the patch is held in place for a predefined amount of time. Suitable are for example 5 sec-5 min. This ensures the patch adapts to the surface of the soft tissue and the fluid interpenetrates both, patch and tissue.

d) The curable monomers within the impregnating fluid are then briefly irradiated or otherwise cured in place. The resulting polymer network spans the patch and suture/stapled site or stoma site and thus fixates the patch on the suture/stapled site or stoma site.

As used herein, the term "immediately after the termination of the incubation period" means within 1 hour, preferably within 30 min, more preferably within 15 minutes, such as less than 10 minutes, preferably less than 5 minutes after the termination of the incubation period.

As used herein, the expression "ready to use in a surgical method" means that the kit of parts claimed and described herein can be directly used in a surgical method i.e. without involving any manufacturing step except for contacting the patch with the impregnating fluid for a period of time defined by the dimensions of the patchprior to application to the sutured site, stapled site or stoma site.

In a further embodiment, the invention relates to the use of said kit of parts and said impregnating fluid as described generally and in any variants herein for veterinary applications.

To further illustrate the invention, the following examples are provided. These examples are provided with no intend to limit the scope of the invention.

All materials used for the examples outlined below were purchased from Sigma-Aldrich (Merck) except N-acryloyl glycinamide which was purchased from Abmole (Belgium). Acrylic acid (AA), methyl acrylate (MA), N-hydroxyl ethyl acrylate (NHEA) and 2-acrylamido-2-methyl-1-propanesulfonic acid) sodium salt (PAMPS) monomers were purified by passing them through a plug of basic alumina (Brockmann Grade I). Acrylamide and N,N'-methylenebisacrylamide (mBAA) were used without further purification. The specific dimensions of the teflon molds that were used for shaping the various components of the patch, e.g. hydrogel support layer, backing layer, encasing sensing matrix, encasing therapeutic matrix are selected based on the intended application and experimental setup. Fresh small intestines were cleaned of its contents manually, divided into pieces and then stored at −20° C. Intestines were preferably used fresh or thawed once and subsequently used for experiments.

1. Preparation of Hydrogel Support Layer

1a. Preparation of a Hydrogel Support Layer Comprising a Non-Degradable P(AAm-MA-AA) Hydrogel First, stock solutions of monomer mixes were prepared and then used to assemble master mixes.

A stock solution of acrylamide (AAm) monomer was made by dissolving the powder in milliQ water at 20 wt %. A 2 wt % crosslinker was made by dissolution of 0.2 g (1.3 mmol) N,N'-methylenebisacrylamide (mBAA) dissolved in 9.8 g Milli-Q water. Both stock solutions were kept for a maximum of 30 days stored at 0-4° C. Stock solutions of curing initiators (photoinitiators) were made fresh before each experiment and kept in the dark. 9.5 mg (42 μmol) 2-hydroxy-4'-(2-hydroxyethoxy)-2-methylpropiophenone (Irgacure 2959) were dissolved in 2 mL Milli-Q water by sonication for 20 min. Previously cleaned monomers were then used to assemble the final hydrogel master mix.

6 mL of AAm monomer stock solution was mixed with 2.28 mL of AA, 1.25 mL of MA, 0.6 mL of photoinitiator Irgacure D-2959 solution and 61.7 μL of mBAA crosslinker stock solution. All constituents were then vortexed in a 15 mL falcon tube. From the resulting mix 300 μL were spread to a Teflon round mold (diameter: 20 mm, depth: 1 mm). The mold was then put under a UVASPOT 400/T mercury lamp at a distance of 30 cm from the source. The light source was equipped with a filter (H2) that allows the spectrum interval from 300 nm until the visible light range to reach the hydrogel mix. The P(AAm-MA-AA) hydrogel was obtained after 180 s irradiation. The resulting hydrogel was then either used directly for further layering or dialyzed against MilliQ water or PBS 4× over 24 h.

1b. Preparation of a Hydrogel Support Layer Comprising a Non-Degradable PAMPS Hydrogel An AMPS monomer mix consisting of 4 mL of 50 wt % of AMPS (aliquoted from the as received stock), 20 μL of mBAA stock and 30.6 μL of Irgacure stock solution, was prepared and used to add 300 μL of this latter to the circular Teflon mold. After allowing the solution to settle for 1 min, the novel layer was polymerized as previously described for 5 min. This formed the suture support layer, typically in contact with the tissue.

2. Preparation of a Backing Layer Comprising a Non-Adhesive Polymer

In case the patch comprises a backing layer, at least three different methods of preparing said backing layer have been used.

2a. Preparation of a Non-Adhesive Polyacrylamide Backing Layer Directly on the Hydrogel Support Layer A 20 wt % acrylamide stock solution of 5 mL was mixed with 108 μL of 2 wt % mBAA crosslinker solution and 500 μL of photoinitiator Irgacure 2959. The resulting prepolymer solution was then cast directly on the top face of the hydrogel support layer and cured under a UVASPOT 400/T mercury lamp as described above.

2b. Preparation of a Separate Non-Adhesive Polyacrylamide Backing Layer for Assembly with the Hydrogel Support Layer A 20 wt % acrylamide stock solution of 5 mL was mixed with 108 μL of 2% mBAA crosslinker solution and 500 μL of photoinitiator Irgacure 2959. The resulting prepolymer solution was then cured independently from the hydrogel support layer under a UVASPOT 400/T mercury lamp as described above. The resulting backing layer was assembled with the hydrogel support layer at a later stage by adding a fresh mix of a prepolymer solution as described above at the interface between the hydrogel support layer and the backing layer (further details in example 5b).

2c. Preparation of a Backing Layer Comprising a Non-Adhesive PNHEA Polymer

A backing layer comprising a non-adhesive PNHEA polymer was prepared in analogy to examples 2a and 2b. 300 μL of a polymerizable stock solution composed of pure, inhibitor removed, 2 mL NHEA monomer, mixed with 2 mL of milliQ water, 53.32 μL of mBAA 2 wt % stock solution and 302 μL of the Irgacure solution (example 1a), the monomer mix was spread on the underlying support layer and left to diffuse in the support layer for 1 min before a 5 min polymerization step. The prepared patches were then kept in the mold and protected from drying using a polyethylene foil until application.

3. Preparation of Patches with Sensing Components

3a. Preparation of an Encasing Sensing Matrix Comprising Gas-Containing Vesicles as Sensing Components for Generating a "Turn-Off" Type Signal by Ultrasound Gas-containing vesicles were presented as milky suspensions in PBS buffer with a typical optical density (OD) of 18. This suspension was then used to dilute acrylamide monomers at 20% vol. An encasing sensing matrix comprising 20% vol gas-containing vesicle as sensing components was made by diluting 1 mL of PBS gas-containing vesicle suspension with 4 mL of MilliQ water. To that is added 1 g of acrylamide, 54 μL of mBAA 2% solution and 8 μL TEMED polymerization accelerator. From the resulting mix, 150 μL were placed in a Teflon mold and polymerization was started by adding 5.8 μL of a 60 mg/mL ammonium persulfate MilliQ water solution. The resulting mixture was placed at 60° C. for 4 min. The resulting opaque white hydrogel was lifted with Teflon tweezers, covered with parafilm to avoid drying and stored at 2-8° C. for further use. The embedded gas-containing vesicles are collapsed upon contact with intestinal fluid ("turn-off" type signal; FIG. 3*b*, FIG. 4*b*).

3b. Preparation of an Encasing Sensing Matrix Comprising Sodium Bicarbonate as Sensing Component for Generating a "Turn-On" Type Signal by Ultrasound A 2 wt % agar water solution was brought to boil and agar was dissolved. To the hot transparent solution was added 2.5 wt % of sodium bicarbonate powder and the mixture was stirred until homogenous under a hot plate. The resulting warm mixture was then cast on round Teflon molds at 50-300 μL increments and left to cool down. At room temperature the resulting gel was used further for incorporation into a 20 wt % AAm imaging phantom. Sodium bicarbonate leads to the generation of gas bubbles upon contact with gastric fluid ("turn-on" type signal; FIG. 4*c*).

3c. Patch Comprising an Alginate Cholate Aerogel (Sensing Component) Encapsulated in a Hydrogel Support Layer Comprising a Synthetic, Non-Degradable Polyurethane Hydrogel:

Alginate Cholate Aerogel (Sensing Component):

A solution of 2M sodium alginate in MilliQ water was created (based on the monomeric units) and mixed with one monomeric equivalent quantity to each of the alginate subunits of sodium cholate. The resulting mix was then divided into 50-500 μL volumes and to each of those was added a 2-20 μL of CaCl2) solution of 0.15M. The resulting hydrogel was then frozen using liquid nitrogen and lyophilized overnight yielding an aerogel that does not mix or get wetted upon prolonged contact with water or gastric fluid. Leak detection using an alginate cholate aerogel is shown in FIG. 11*a*.

Incorporation of sensing component into hydrogel support layer: The resulting material (alginate cholate aerogel) was then placed on a rectangular 5×1.5×0.2 cm Teflon mold. To this was added 1500 μL of a solution comprising a polymerizable mix composed of 4 mL of 50 wt % 2-acrylamido-2-methyl-1-propanesulfonic acid sodium salt solution, 20 μL N,N'-Methylenebis(acrylamide) 2 wt. % and 30.6 μL 4.825 mg/mL Irgacure 2959 initiator. Upon polymerization the resulting patches are coated with 1500 μL of 20 wt % Hydromed D4 (ether based hydrophilic polyurethane) in a solution of 95% ethanol and 5% water. The resulting patches, upon drying of the backing polyurethane layer are then ready for interaction with biological fluids.

3d. Patch Comprising Silica Aerogel Particles (Sensing Component) Encapsulated in a Hydrogel Support Layer Comprising a Synthetic, Non-Degradable Polyurethane:

Similarly to the alginate cholate aerogel described in example 3c, commercial superhydrophobic silica aerogel particles (Lumira-Aerogel technologies LLC) were used as a contrast changing substance (sensing component for detecting a biliary leak; FIG. 11*b*).

10-100 mg (depending on the size of the patch to be made) of Lumira superhydrophobic silica aerogel particles were placed within a PAMPS hydrogel (hydrogel support layer; 1500 μL of a stock solution composed of 4 mL of 50 wt. % 2-acrylamido-2-methyl-1-propanesulfonic acid sodium salt solution, 20 μL N,N'-Meth-ylenebis(acrylamide) 2 wt. % and 30.6 μL 4.825 mg/mL Irgacure 2959 initiator). This construct was then fused together using 20 wt % Hydromed D4 (ether based hydrophilic polyurethane) in a solution of 95% ethanol and 5% water (backing layer). The resulting patch (silica aerogel particles being semi-encapsulated in the hydrogel support layer; backing layer containing polyurethane) was stored in a fitting chamber at 40° C. in order to evaporate residual ethanol.

3e. Patch Comprising $Ta_2O_5$ Nanoparticles as CT Sensing Components Embedded in a Hydrogel Support Layer Comprising PAMPS A polymerizable mix composed of 2-acrylamido-2-methyl-1-propanesulfonic acid gel mixture of 4 mL of 50 wt. % 2-acrylamido-2-methyl-1-propanesulfonic acid sodium salt solution was combined with 20 μL N,N'-Methylenebis (acrylamide) 2 wt. % and 30.6 μL 4.825 mg/mL Irgacure 2959 initiator. The resulting mix was combined with $Ta_2O_5$ nanoparticle powder at 5 wt %. The suspension was vigorously vortexed, placed on a Teflon mold at increments of 10-150 μL and polymerized under a UV lamp (2×6 W-365 nm VL-206.BL lamp)

3f. Patch Comprising $Ta_2O_5$ Nanoparticles as CT Sensing Components Embedded in a Hydrogel Support Layer Comprising PNAGA A N-acryloyl glycinamide polymerizable mix composed of: 2 g N-acryloyl glycinamide, dissolved in 4 mL milliQ water alongside 450 μL 6.33 mg/mL Lithium phenyl-2,4,6-trimethylbenzo-ylphosphinate was prepared. The resulting mix was combined with Ta2O5 nanoparticle powder at 5 wt %. The suspension was vigorously vortexed, placed on a Teflon mold at increments of 10-150 μL and polymerized under a UV lamp (2×6 W-365 nm VL-206.BL lamp)

3 g. Encasing Sensing Matrix Comprising CaCO3 (Sensing Component for CT and Ultrasound Imaging)

A 2 wt % agar water solution was brought to boil and agar was dissolved. To the hot transparent solution was added 35 wt % of calcium carbonate powder and the mixture was stirred until homogenous under a hot plate. Each sample was cooled under stirring until viscous and then left covered at room temperature in order to fully solidify. With the use of a biopsy punch, small circular disks were cut out of each sample and further processed into patches. Calcium carbonate leads to the generation of gas bubbles upon contact with gastric fluid ("turn-on" type signal; FIG. 4*c*) but also the generation of a computer tomography iden-tifiable signal.

4a. Preparation of an Encasing Therapeutic Matrix Comprising ZnO Nanoparticles as Therapeutic Component The encasing therapeutic matrix comprising ZnO nanoparticles as therapeutic component was prepared in analogy to the above described preparation of an encasing sensing matrix comprising gas-containing vesicles as sensing components. In more detail, flame spray pyrolysis synthesized ZnO nanoparticles were sus-pended in a 20 wt % acrylamide solution at a concentration of 2.5 mg/mL. For a 5 mL stock solution 54 μL of mBAA 2% solution and 8 μL TEMED polymerization accelerator were added and mixed. The resulting (prepolymer) solution was placed under sonication in order to homogenously disperse the particles in the (prepolymer) mixture. 150 μL of this mixture were placed in a Teflon mold. Then, polymerization was started by adding 5.8 μL of a 60 mg/mL ammonium persulfate MilliQ water solution and the mixture was placed at 60° C. for 4 min. The resulting opaque white hydrogel was lifted with Teflon tweezers, covered with parafilm to avoid drying and stored at 2-8° C. for further use.

4b. Preparation of an Encasing Therapeutic Matrix Comprising Gentamycin as Therapeutic Component A 50 mg/mL gentamicin solution as obtained from Sigma was diluted to 1 mg/mL using a polymerizable mix of 5 mL of 20 wt % Acrylamide, 500 μL 4.825 mg/mL 12959 (or 500 μL 6.33 mg/mL LAP) 64.8 μL mBAA 2 wt %. The resulting mix was used to add increments of 10-300 μL volumes to a Teflon mold. The resulting encasing therapeutic matrix comprising gentamycin was incorporated into the patch as described in example 5k.

5. Assembly of the Patch

The following embodiments of the patch are implemented.

5a. Assembly of a Patch Comprising a Hydrogel Support Layer and a Backing Layer Wherein the Backing Layer is Prepared Directly on the Hydrogel Support Layer To form a patch comprising a hydrogel support layer and a backing layer, liquid backing monomer mix, as described above was directly added to the hydrogel support layer. The construct was then irradiated for 3 min under UV light. The resulting patch may then either be used directly, e.g. as a tissue sealant or be dialyzed against MilliQ water or PBS.

5b. Assembly of a Patch Comprising a Hydrogel Support Layer and a Backing Layer Wherein a Separately Prepared Backing Layer is Used To form a patch comprising a hydrogel support layer and a backing layer, a separately prepared backing layer (described above) was added to the hydrogel support layer (described above) and the prepolymer solution used to make the separate backing layer was applied at the connecting interfaces of each individual component. The construct is then irradiated for 3 min under UV light. The resulting patch may then either be used directly, e.g. as a tissue sealant or be dialyzed against MilliQ water or PBS.

5c. Assembly of a Patch Comprising a Hydrogel Support Layer, a Backing Layer, and a Sensing Component and/or a Therapeutic Component Wherein the Sensing Component is Placed Inside Holes of the Hydrogel Support Layer and the Backing Layer is Pre-pared Directly on the Hydrogel Support Layer To form a patch comprising a hydrogel support layer, a backing layer and a sensing component and/or a therapeutic component, the hydrogel support layer was patterned with surgical biopsy punches of 4-8 mm diameter. The sensing components (gas-containing vesicles as described above) and/or therapeutic components were placed into the created holes and fitted to the pattern created. The resulting combined layer (hydrogel support layer and sensing component and/or therapeutic component) was then fused together by using a liquid backing monomer mix, as described above. The construct was then irradiated for 3 min under UV light. The resulting patch may then either be used directly, e.g. as a tissue sealant or be dialyzed against MilliQ water or PBS and then used to as a sealant via impregnation with curable impregnating fluid.

5d. Assembly of a Patch Comprising a Hydrogel Support Layer, a Backing Layer, and a Sensing Component Wherein the Sensing Component is Placed Inside Holes of the Hydrogel Support Layer and a Separately Prepared Backing Layer is Used To form a patch comprising a hydrogel support layer, a backing layer, and a sensing component, the hydrogel support layer was patterned with surgical biopsy punches of 4-8 mm diameter. The sensing components (gas-containing vesicles as described above) were placed into the created holes and fitted to the pattern created. The resulting combined layer (hydrogel support layer and sensing component) was then fused together by adding a separately prepared backing layer (described above) and by applying the prepolymer solution used to make the separate backing layer at the connecting interfaces of each individual component. The construct was then irradiated for 3 min under UV light. The resulting patch may then either be used directly, e.g. as a tissue sealant or be dialyzed against MilliQ water or PBS.

5e. Assembly of a Patch Comprising a Hydrogel Support Layer, a Backing Layer, and a Sensing Component Wherein the Sensing Component is Placed on Top of the Hydrogel Support Layer and the Backing Layer is Prepared Directly on the Hydrogel Support Layer To form a patch comprising a hydrogel support layer, a backing layer, and a sensing component, the sensing components (synthetic gas-containing microbubbles or gas-containing vesicles or gas generating compounds as described above) were placed directly on the hydrogel support layer. The resulting combined layer (hydrogel support layer and sensing component) was then fused together by using a liquid backing monomer mix, as described above. The construct was then irradiated for 3 min under UV light. The resulting patch may then either be used directly, e.g. as a tissue sealant or be dialyzed against MilliQ water or PBS.

5f. Assembly of a Patch Comprising a Hydrogel Support Layer, a Backing Layer, and a Sensing Component Wherein the Sensing Component is on Top of the Hydrogel Support Layer and a Separately Prepared Backing Layer is Used To form a patch comprising a hydrogel support layer, a backing layer, and a sensing component, the sensing components (gas-containing vesicles as described above) were placed directly on the hydrogel support layer. The resulting combined layer (hydrogel support layer and sensing component) was then fused together by adding a separately prepared backing layer (described above) and by applying the prepolymer solution used to make the separate backing layer at the connecting interfaces of each individual component. The construct was then irradiated for 3 min under UV light. The resulting patch may then either be used directly, e.g. as a tissue sealant or be dialyzed against MilliQ water or PBS.

5 g. Assembly of a Patch Comprising a Hydrogel Support Layer, a Backing Layer, and a Therapeutic Component Wherein the Therapeutic Component is Placed Inside Holes of the Hydrogel Support Layer and the Backing Layer is Prepared Directly on the Hydrogel Support Layer To form a patch comprising a hydrogel support layer, a backing layer, and a therapeutic component, the hydrogel support layer was patterned with surgical biopsy punches of 4-8 mm diameter. The therapeutic component (ZnO as described above or gentamycin as described above) was placed into the created holes and fitted to the pattern created. The resulting combined layer (hydrogel support layer and therapeutic component) was then fused together by using a liquid backing monomer mix, as described above. The construct was then irradiated for 3 min under UV light. The resulting patch may then either be used directly, e.g. as a tissue sealant or be dialyzed against MilliQ water or PBS.

5 h. Assembly of a Patch Comprising a Hydrogel Support Layer, a Backing Layer, and a Therapeutic Component Wherein the Therapeutic Component is Placed Inside Holes of the Hydrogel Support Layer and a Separately Prepared Backing Layer is Used To form a patch comprising a hydrogel support layer, a backing layer, and a therapeutic component, the hydrogel support layer was patterned with surgical biopsy punches of 4-8 mm diameter. The therapeutic component (ZnO as described above or gentamycin as described above) was placed into the created holes and fitted to the pattern created. The resulting combined layer (hydrogel support layer and sensing component) was then fused together by adding a separately prepared backing layer (described above) and by applying the prepolymer solution used to make the separate backing layer at the connecting interfaces of each individual component. The construct was then irradiated for 3 min under UV light. The resulting patch may then either be used directly, e.g. as a tissue sealant or be dialyzed against MilliQ water or PBS.

5i. Assembly of a Patch Comprising a Hydrogel Support Layer, a Backing Layer, and a Therapeutic Component Wherein the Therapeutic Component is Placed on Top of the Hydrogel Support Layer and the Backing Layer is Prepared Directly on the Hydrogel Support Layer To form a patch comprising a hydrogel support layer, a backing layer, and a therapeutic component, the therapeutic component (ZnO as described above) was placed directly on the hydrogel support layer. The resulting combined layer (hydrogel support layer and therapeutic component) was then fused together by using a liquid backing monomer mix, as described above. The construct was then irradiated for 3 min under UV light. The resulting patch may then either be used directly, e.g. as a tissue sealant or be dialyzed against MilliQ water or PBS.

5j. Assembly of a Patch Comprising a Hydrogel Support Layer, a Backing Layer, and a Therapeutic Component Wherein the Therapeutic Component is on Top of the Hydrogel Support Layer and a Separately Prepared Backing Layer is Used To form a patch comprising a hydrogel support layer, a backing layer, and a therapeutic component, the therapeutic component (ZnO as described above or gentamycin) was placed directly on the hydrogel support layer. The resulting combined layer (hydrogel support layer and sensing component) was then fused together by adding a separately prepared backing layer (described above) and by applying the prepolymer solution used to make the separate backing layer at the connecting interfaces of each individual component. The construct was then irradiated for 3 min under UV light. The resulting patch may then either be used directly, e.g. as a tissue sealant or be dialyzed against MilliQ water or PBS.

5k. Assembly of a Patch Comprising a Hydrogel Support Layer, a Backing Layer, and a Functional Component, Wherein the Functional Component is Embedded in an Additional Layer (Referred to as Encasing Sensing and/or Therapeutic Matrix)

A patch comprising a hydrogel support layer, a backing layer, and a functional component comprised within an additional layer (encasing sensing and/or therapeutic matrix) was formed by combining a hydrogel support layer, an additional layer comprising a functional component, and a backing layer. The layers were prepared and fused together in analogy to the procedures described above.

6. Application of Kit of Parts on Tissue—Sealing Properties

Kit of parts comprising a patch and an impregnating fluid as described above were applied ex vivo on porcine small intestine serosa. A hole was created in the small intestine serosa to simulate the opening through which a biological fluid would leak in case of e.g. anastomotic leakage. A patch as described above was immersed for 10 min in an impregnating fluid comprising the same curable monomers as were used to form the hydrogel support layer, in a flat, closed petri dish. At the same time, the intestine serosa was brought in contact with 150 μL of the impregnating fluid, around the area of intended application of the patch (excluding the area of the (4 mm) hole). The impregnated patch was then applied to the intestine with attention to not include air bubbles at the interface with the tissue as well as to not lift the patch once in place. The patch tissue construct was held in place with optically transparent plastic removable supports, ensuring good positioning and absence of folds. The samples were then subjected to 180 see of low dose UV irradiation. In order to mitigate tissue heating and drying, the samples were placed on an aluminium foil containing a crushed ice bed.

7. Application of Kit of Parts on Tissue—Influence of Impregnating Fluid on Adhesion Properties The influence of the impregnating fluid on the adhesion strength of the patch to soft tissue was investigated using two identical patches, each consisting of a hydrogel support layer containing a non-degradable PAMPS hydrogel (example 1b) and a backing layer containing a non-adhesive PNHEA polymer (example 2c).

These patches were prepared using first an AMPS monomer mix consisting of 4 mL of 50 wt % of AMPS (aliquoted from the as received stock), 20 μL of mBAA stock and 30.6 μL of Irgacure stock solution. This polymerizable mix was prepared and used to add 1500 μL of this latter to a 7×1.5×0.2 cm Teflon mold. The layer was polymerized as previously described for 5 min. The same procedure was followed for the formation of the backing. Thus, using a 1500 μL backing mix coming from a polymerizable stock solution composed of pure, inhibitor removed, 2 mL NHEA monomer, mixed with 2 mL of milliQ water, 53.32 μL of mBAA 2 wt % stock solution and 302 μL of the previously prepared Irgacure solution, the monomer mix was spread on the underlying support layer and left to diffuse in the support layers for 1 min before a 5 min polymerization step. The prepared patches were then kept in the mold and protected from drying using a polyethylene foil until application.

Porcine small intestine was used as an exemplary soft tissue. Measurements were conducted according to ASTM standard F 2256-05 (T peel test; FIG. 8). In one case, the patch was impregnated with the impregnating fluid (6 mL polymerizable stock: 2 g NAGA, 4 mL milliQ water, 450 μL 6.33 mg/mL LAP) immediately before application on the tissue as described in example 6 (indicated as (I) in FIG. 8). In the other case, the impregnating fluid (same as for (I, 1.5 mL of water solution of 33 wt % NAGA monomer mix with 6.33 mg/mL LAP initiator) was applied to the patch and cured prior to application on the tissue (indicated as (II) in FIG. 8).

Porcine small intestine was cut into pieces of 7 cm×1.5 cm using a scalpel after being thawed at room temperature. In order to limit the deformation of the gel and tissue, rigid transparent films (CG3720 color laser transparency film, 3M) were used as a stabilisation liner. The rigid films were cut to the size of the patches (5 cm×1.8 cm×0.1 cm) and were attached to one side of the intestine pieces using a liquid superglue (Pattex Super Glue). The patches were then applied to the intestine pieces. As described above, in one case the impregnating fluid was applied to the patch and cured prior to application on the tissue and in the other case the impregnating fluid was applied to the patch immediately before application on the tissue and cured after application of the patch on the tissue.

The free ends of the patches and the intestine piece were loaded to the instrument's clamps. The loading rate was kept constant at 250 mm/min and the standard force-strain curves were recorded. The T peel strength was calculated as the maximum plateau value of the ratio between the standard force and width of the sample (FIG. 8).

8. Preparation of Impregnating Fluid.

8a. Preparation of an Impregnating Fluid Comprising AAm, MA and AA Curable Monomer A stock solution of acrylamide (AAm) monomer was made by dissolving the powder in milliQ water at 20 wt %. A 2 wt % crosslinker was made by dissolution of 0.2 g (1.3 mmol) N,N'-methylenebisacrylamide (mBAA) dissolved in 9.8 g Milli-Q water. Both stock solutions were kept for a maximum of 30 days stored at 0-4° C. Stock solutions of curing initiators (photoinitiators) were made fresh before each experiment and kept in the dark. 9.5 mg (42 μmol) 2-hydroxy-4'-(2-hydroxyethoxy)-2-methylpropiophenone (Irgacure 2959) were dissolved in 2 mL Milli-Q water by sonication for 20 min. Previously cleaned monomers were then used to assemble the final hydrogel master mix.

6 mL of AAm monomer stock solution was mixed with 2.28 mL of AA, 1.25 mL of MA, 0.6 mL of photoinitiator Irgacure D-2959 solution and 61.7 μL of mBAA crosslinker stock solution. All constituents were then vortexed in a 15 mL falcon tube.

The resulting polymerizable mix was used as impregnating fluid.

8b. Preparation of an Impregnating Fluid Comprising NAGA Curable Monomers

In analogy to the procedure described in example 8a, an impregnating fluid was prepared as 1.5 mL of water solution of 33 wt % NAGA monomer mix with 6.33 mg/mL LAP initiator.

9. Tensile Strength Measurements—Influence of Backing Layer

Using custom dumbbell-shaped Teflon molds 4.5 cm in length and 0.5 cm in width tensile property tests of the various layers of the investigated patches were tested. Sample volumes were kept equal and layer volumes were adjusted to maintain comparable final sample sizes. The tensile properties were thus measured with a mechanical testing machine (Zwick/Roell Z100 (Zwick/Roell, Ulm, Germany)). All tests were done at a constant tensile speed of 5 mm/min. At least three independent experiments were carried out per experimental group. Results are shown in FIG. 9.

10. Penetration of Impregnating Fluid into Patch and Tissue—Formation of a Mutually Interpenetrating Network Hydrogel application: Hydrogels that were prepared as previously described were immersed for 10 min in 1.5 mL of water solution of 33 wt % NAGA monomer mix with 6.33 mg/mL LAP initiator. The incubation was performed, in a 10 mL, plastic cup topped by a second plastic cup of the same size, to avoid drying and hydrogel curling. After the incubation time of the gel was completed the tissue serosa was brought in contact with (150 μL) of polymerizable fluid mix, at the area of application of the hydrogel (excluding the area of the (4 mm) hole). The swollen hydrogels were then applied to the intestine making sure that no bubbles were trapped at the interface. Once in place a transparent glass plate was used to assure firm contact of the gel with the tissue surface and the samples were then subjected to 5 min of visible light irradiation using a 2×6 W-365 nm VL-206.BL lamp.

Mutually interpenetration properties of the network into the hydrogel patch and the tissue were characterized by label-free vibrational spectroscopy (FTIR and Raman).

Infrared absorption spectra of the mIPN penetrated hydrogel patch and reference samples were measured using a Varian 640-IR spectrometer equipped with diamond attenuated total reflectance (ATR) optics from as prepared hydrogel samples. The hydrogels were flipped on the crystal to record the spectrum of each layer in the case of layered hydrogels.

Raman measurements: Raman measurements were performed on depar-affinized histological sections on a WITec alpha 300R confocal Raman microscope, equipped with a UHTS 300 Vis spectrometer and an Andor Newton EMCCD. A linearly polar-ized 532 nm laser and a laser power of 5 mW were used for excitation. A Zeiss EC Epiplan Neofluar Dic 50× objective (NA 0.8) was used. Spectra were acquired with an integration time of 2 s with a step size of 2 μm and in maps of size (50×150 μm2), starting at the outer surface of the intestinal sample. Three maps from different regions were recorded per sample. The preprocessed (cosmic ray removed and background-substracted) spectra were subjected to k-means clustering analysis (Control Four Software, WITec). Cluster maps for the tissue cluster featuring characteristic bands at 1003 $cm^{-1}$, 1448 $cm^{-1}$ and 1655 $cm^{-1}$ and the mIPN cluster featuring a unique peak at 860 $cm^{-1}$, are displayed and used to assess mIPN tissue penetration. Results are shown in FIG. 10.

The invention claimed is:

1. A kit of parts ready to use in a surgical method comprising a first part and a second part, wherein the first part is a shaped article in the form of a patch for application on a sutured site, a stapled site or a stoma site of a subject in need thereof, the patch comprising a hydrogel support layer, optionally a backing layer, and optionally functional components selected from sensing components, and therapeutic components, and the second part is an impregnating fluid for application on a sutured site, a stapled site or a stoma site of a subject in need thereof, and on the patch, wherein the impregnating fluid comprises a pharmaceutically acceptable liquid, curable monomers, optionally curing initiators, and optionally additives;

wherein the curable monomers present in the impregnating fluid are in an uncured, monomeric state when the impregnating fluid is not applied on the patch, and wherein the hydrogel support layer comprises a non-degradable, synthetic hydrogel; and the optional backing layer comprises a non-adhesive polymer; and the liquid is selected from water and/or glycerol; and the optional curing initiator is adapted for curing the curable monomers; and the patch and the impregnating fluid are each separately packed for transport and/or sale and prior to the use in a surgical method; and the patch is impregnated with the fluid shortly before application on a tissue, such that curing of the monomers that are present in the impregnating fluid is initiated after application of the patch.

2. The kit according to claim 1, wherein the hydrogel support layer comprises a non-degradable, synthetic hydrogel comprising monomeric units selected from the group consisting of methacrylates, acrylates, vinyls, thiols, polyurethane forming monomers, and mixtures thereof.

3. The kit according to claim 1, wherein the backing layer is present and the non-adhesive polymer is selected from the group consisting of synthetic polymers comprising monomeric units selected from the group consisting of methacrylates, acrylates, vinyls, thiols, polyurethane forming monomers, and mixtures thereof; and/or natural polymers, and/or acrylated natural polymers.

4. The kit according to claim 1, wherein the impregnating fluid comprises:

curable monomers selected from the group consisting of methacrylates, acrylates, vinyls, thiols, and mixtures thereof, and optionally curing initiators selected from the group consisting of photoinitiators, oxidizing curing initiators, radical generators, enzymes or heat-activatable curing initiators.

5. The kit according to claim 1, wherein the patch further comprises functional components that are sensing components, the sensing components being present either in the hydrogel support layer and/or in the backing layer, or in an additional layer of the patch; and the sensing components being selected from the group consisting of synthetic gas-containing microbubbles and/or gas-containing vesicles, and/or carbonates and/or inorganic nanoparticles and/or hydrophobic aerogels.

6. The kit according to claim 1, wherein the patch further comprises functional components that are therapeutic components, the therapeutic components being present either in the hydrogel support layer and/or in the backing layer, or in an additional layer of the patch;

the therapeutic components being selected from the group consisting of antimicrobials, growth factors, flavonoids, metal oxide nanoparticles, alginate, and peptides.

7. The kit according to claim 1, wherein the impregnating fluid comprises additives, the additives being selected from the group consisting of transglutaminase;

ionic strength adjusting media, including buffers and salts; and surface active substances, including non-ionic, cationic, anionic and amphoteric surfactants.

8. The kit according to claim 1, wherein in a first embodiment the patch consists of a hydrogel support layer;

the hydrogel support layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine; and the curable monomers of the impregnating fluid are selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine; or in a second embodiment the patch consists of a hydrogel support layer and a backing layer;

the hydrogel support layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine;

the backing layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine; and/or one or more natural polymers selected from the group consisting of carboxymethylcellulose, and alginate; and the curable monomers of the impregnating fluid are selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl) methyl acrylamide, bis-acrylamide, poly ethylene glycol diacrylate, and N,N'-bis (acryloyl) cystamine; or in a third embodiment the patch consists of a hydrogel support layer, a backing layer, and sensing components;

the hydrogel support layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-Tris (hydroxymethyl) methyl acrylamide, bis-acrylamide, poly ethylene glycol diacrylate, and N,N'-bis (acryloyl) cystamine;

the backing layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine and/or one or more natural polymers selected from the group consisting of carboxy methyl-cellulose, and alginate;

the sensing components are selected from the group consisting of $NaHCO_3$, $Na_2CO_3$, $CaCO_3$, gas-containing vesicles and/or synthetic gas-containing microbubbles, iron oxide nanoparticles, and zinc oxide nanoparticles; and the curable monomers of the impregnating fluid are selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine; or in a fourth embodiment the patch consists of a hydrogel support layer, a backing layer, sensing components, and therapeutic components;

the hydrogel support layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine;

the backing layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine and/or one or more natural polymers selected form the group consisting of carboxymethylcellulose and alginate;

the sensing components are selected from the group consisting of $NaHCO_3$, $Na_2CO_3$, $CaCO_3$, gas-containing vesicles and/or synthetic gas-containing microbubbles, iron oxide nanoparticles, and zinc oxide nanoparticles;

the therapeutic components are selected from the group consisting of antimicrobials and compounds that support wound healing; and the curable monomers of the impregnating fluid are selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine; or in a fifth embodiment the patch consists of a hydrogel support layer, a backing layer, and therapeutic components;

the hydrogel support layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine;

the backing layer comprises monomeric units selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine and/or one or more natural polymers selected form the group consisting of carboxymethylcellulose and alginate;

the therapeutic components are selected from the group consisting of antimicrobials and compounds that support wound healing; and the curable monomers of the impregnating fluid are selected from the group consisting of acrylamide, acrylic acid, methyl acrylate, 2-hydroxyethyl acrylate, 2-hydroxyethyl acrylamide, sodium 2-acrylamido-2-methylpropane sulfonate, N-acryloyl glycinamide, styrene sulfonate, N-tris (hydroxymethyl) methyl acrylamide, bis-acrylamide, poly ethylene glycol diacrylate, and N,N'-bis (acryloyl) cystamine.

9. The kit according to claim 1, wherein the patch in a first embodiment consists of a hydrogel support layer and a backing layer; and the hydrogel support layer comprises one or more groups of the functional components; or in a second embodiment consists of a hydrogel support layer and a backing layer;

the hydrogel support layer comprises one group of the functional components; and the backing layer comprises another group of the functional components; or in a third embodiment consists of a hydrogel support layer, a backing layer and an additional layer; and the additional layer comprises one or more groups of the functional components; or in a fourth embodiment consists of a hydrogel support layer and a backing layer;

the hydrogel support layer comprises one or more groups of the functional components; and the backing layer comprises one or more groups of the functional components.

10. The kit according to claim 1, wherein the patch comprises a hydrogel support layer and a backing layer, wherein the non-degradable, synthetic hydrogel is poly (2-acrylamido-2-methyl-1-propanesulfonic acid);

the non-adhesive polymer is poly (N-hydroxyethyl-acrylamide) or a hydrophilic polyurethane;

the curable monomers are N-acryloyl glycinamide monomers; and the pharmaceutically acceptable liquid is water.

11. The kit according to claim 1, wherein the patch has a shape selected from cylindrical, rectangular, rhombohedral, trapezoidal and triangular shape; and/or has dimensions in the range of 0.5-40 mm thickness, 5-15000 mm length and 5-10000 mm width.

12. A process for manufacturing a kit according to claim 1, wherein the patch is manufactured by a) providing a solution comprising monomers that are part of the hydrogel support layer and a curing initiator adapted for curing the monomers, b) subjecting the solution to a 3D-printing or mold-curing step to thereby obtain a sheet-like material, c) optionally cutting the thus obtained sheet like material to obtain a patch, and d) packaging the patch; and wherein the impregnating fluid is manufactured by combining the pharmaceutically acceptable liquid, the curable monomers, optionally curing initiators, and optionally additives to obtain a fluid and packaging the fluid.

13. The kit of parts according to claim 1, wherein the surgical method comprises the steps of a) contacting the patch with the impregnating fluid; and then b) contacting the sutured site, stapled site or stoma site with the impregnating fluid; and then c) applying the patch to the sutured site or stapled site or stoma site d) curing the curable monomers within the impregnating fluid.

14. An impregnating fluid for use in a surgical method for adhering a patch to a sutured site, a stapled site or a stoma site of a subject in need thereof, wherein the impregnating fluid comprises a pharmaceutically acceptable liquid selected from water and/or glycerol; and curable monomers;

the curable monomers present in the impregnating fluid are in an uncured, monomeric state when the impregnating fluid is not applied on the patch; and the patch comprises a hydrogel support layer comprising a non-degradable, synthetic hydrogel.

15. The impregnating fluid for use according to claim 14 wherein the surgical method comprises a method of artificial stoma seal.

* * * * *